US012561860B2

(12) United States Patent
Arden

(10) Patent No.: US 12,561,860 B2
(45) **Date of Patent: \*Feb. 24, 2026**

(54) SYSTEM AND METHOD FOR IMPROVED DATA STRUCTURES AND RELATED INTERFACES

(71) Applicant: THE ALCHEMY OF YOU, LLC, New York, NY (US)

(72) Inventor: Allison Arden, New York, NY (US)

(73) Assignee: The Alchemy of You, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/600,058

(22) Filed: Mar. 8, 2024

(65) Prior Publication Data

US 2024/0233219 A1 Jul. 11, 2024

Related U.S. Application Data

(63) Continuation of application No. 17/335,739, filed on Jun. 1, 2021, now Pat. No. 11,935,164, which is a
(Continued)

(51) Int. Cl.
*G16H 10/20* (2018.01)
*G06F 3/0482* (2013.01)
(Continued)

(52) U.S. Cl.
CPC .......... *G06T 11/206* (2013.01); *G06T 11/001* (2013.01); *G16H 10/20* (2018.01); *G06F 3/0482* (2013.01); *G06T 2200/24* (2013.01)

(58) Field of Classification Search
CPC . G06T 11/206; G06T 11/001; G06T 2200/24; G16H 10/20; G16H 20/70; G06F 3/0482
See application file for complete search history.

(56) References Cited

U.S. PATENT DOCUMENTS

2013/0282618 A1* 10/2013 Dunn ..................... G06Q 40/06
705/36 R
2014/0095150 A1* 4/2014 Berjikly .................. G06F 40/40
704/9

(Continued)

*Primary Examiner* — Jitesh Patel
(74) *Attorney, Agent, or Firm* — Brooks Kushman, P.C.

(57) ABSTRACT

The present disclosure relates to a computer-implemented method and system for improvements to emotional and behavioral interfaces. In an example, a first group of color-coded regions is displayed representing emotions and behaviors for data collected from one or more participants using an input method. Correspondences are determined within the first group of color-coded regions. Individuals ones of the first group of color-coded regions are provided with a first portion of pixels in a first color associated with a value in the date based in part on the correspondences. A second portion of pixels is provided with a second color associated with a neutral indication. Changes to the data over discrete or random intervals of time are determined as modifying the correspondences. A dynamical change is applied to the first portion of pixels and the second portion of pixels to update the display of the first group of color-coded regions.

20 Claims, 17 Drawing Sheets

Related U.S. Application Data continuation of application No. 16/582,698, filed on Sep. 25, 2019, now Pat. No. 11,049,299.

(60) Provisional application No. 62/736,661, filed on Sep. 26, 2018.

(51) Int. Cl.
  *G06T 11/00* (2006.01)
  *G06T 11/20* (2006.01)

(56) References Cited

U.S. PATENT DOCUMENTS

| | | | | |
|---|---|---|---|---|
| 2014/0099610 | A1* | 4/2014 | Bak | G09B 19/00 |
| | | | | 434/236 |
| 2015/0078632 | A1 | 3/2015 | Hachisuka et al. | |
| 2015/0213002 | A1* | 7/2015 | Gou | G06F 40/30 |
| | | | | 704/9 |
| 2015/0268098 | A1 | 9/2015 | Minchew et al. | |
| 2015/0356160 | A1* | 12/2015 | Berwick | G06F 3/04817 |
| | | | | 715/781 |
| 2015/0358415 | A1 | 12/2015 | Cronin | |
| 2015/0379888 | A1 | 12/2015 | Hill | |
| 2016/0026738 | A1* | 1/2016 | Gou | G06Q 30/0204 |
| | | | | 703/2 |
| 2016/0165003 | A1 | 6/2016 | Blattner | |
| 2016/0231882 | A1* | 8/2016 | Berliner | G06F 16/22 |
| 2017/0092148 | A1 | 3/2017 | Uno | |
| 2017/0143246 | A1 | 5/2017 | Flickinger | |
| 2017/0228745 | A1* | 8/2017 | Garcia | G06Q 30/0203 |
| 2017/0311861 | A1 | 11/2017 | Pan et al. | |
| 2018/0101238 | A1 | 4/2018 | Yin et al. | |
| 2018/0101239 | A1* | 4/2018 | Yin | G06F 3/011 |
| 2018/0130459 | A1 | 5/2018 | Paradiso et al. | |
| 2018/0267759 | A1 | 9/2018 | Llewelyn | |

* cited by examiner

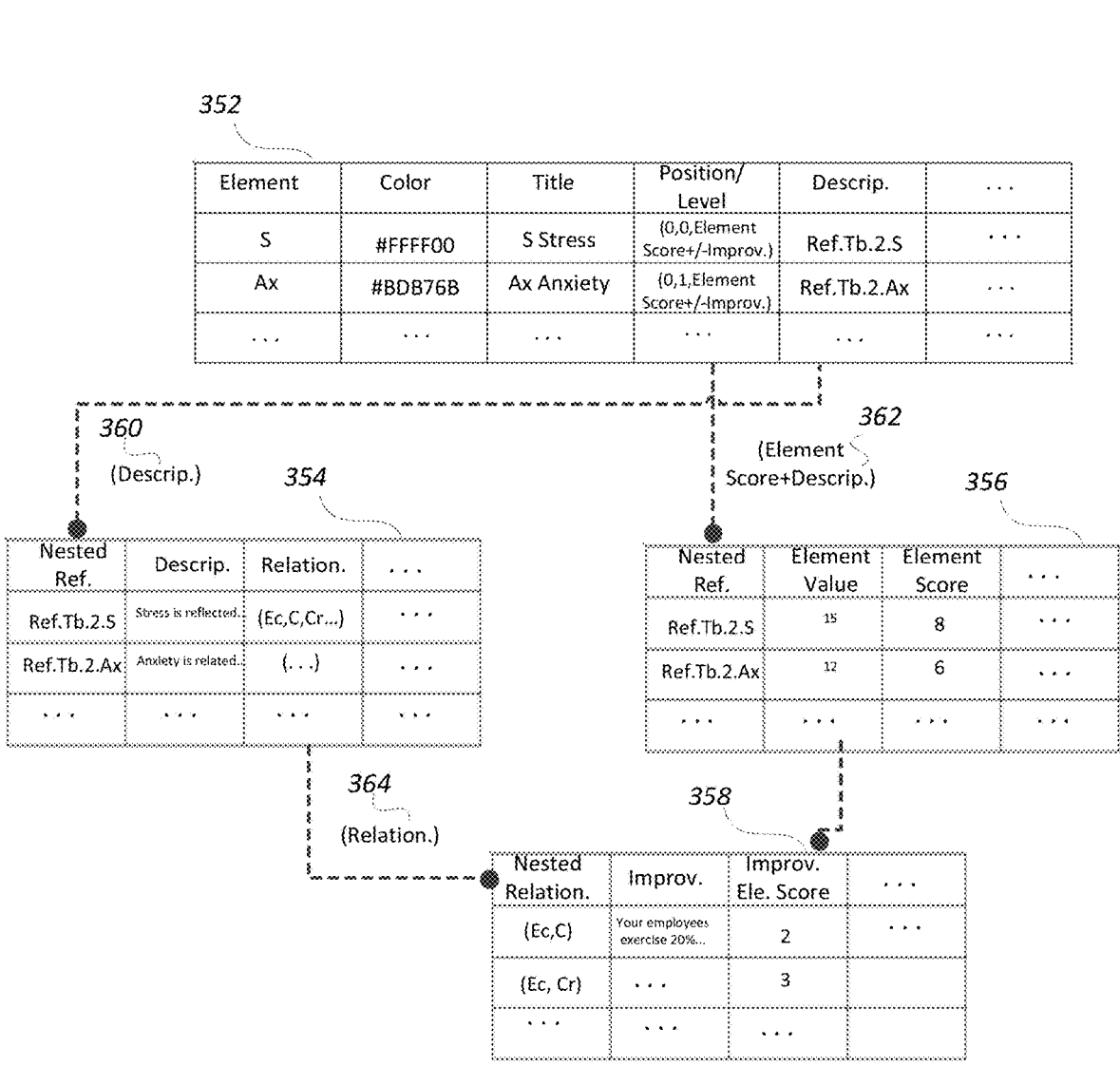

*350*

*352*

| Element | Color | Title | Position/ Level | Descrip. | . . . |
|---------|-------|-------|-----------------|----------|-------|
| S | #FFFF00 | S Stress | (0,0,Element Score+/-Improv.) | Ref.Tb.2.S | . . . |
| Ax | #BDB76B | Ax Anxiety | (0,1,Element Score+/-Improv.) | Ref.Tb.2.Ax | . . . |
| . . . | . . . | . . . | . . . | . . . | . . . |

*360*

(Descrip.)

*362*

(Element Score+Descrip.)

*354*

*356*

| Nested Ref. | Descrip. | Relation. | . . . |
|-------------|----------|-----------|-------|
| Ref.Tb.2.S | Stress is reflected. | (Ec,C,Cr...) | . . . |
| Ref.Tb.2.Ax | Anxiety is related. | (...) | . . . |
| . . . | . . . | . . . | . . . |

| Nested Ref. | Element Value | Element Score | . . . |
|-------------|---------------|---------------|-------|
| Ref.Tb.2.S | 15 | 8 | . . . |
| Ref.Tb.2.Ax | 12 | 6 | . . . |
| . . . | . . . | . . . | . . . |

*364*

(Relation.)

*358*

| Nested Relation. | Improv. | Improv. Ele. Score | . . . |
|------------------|---------|--------------------|-------|
| (Ec,C) | Your employees exercise 20%... | 2 | . . . |
| (Ec, Cr) | . . . | 3 | |
| . . . | . . . | . . . | |

FIG. 3C

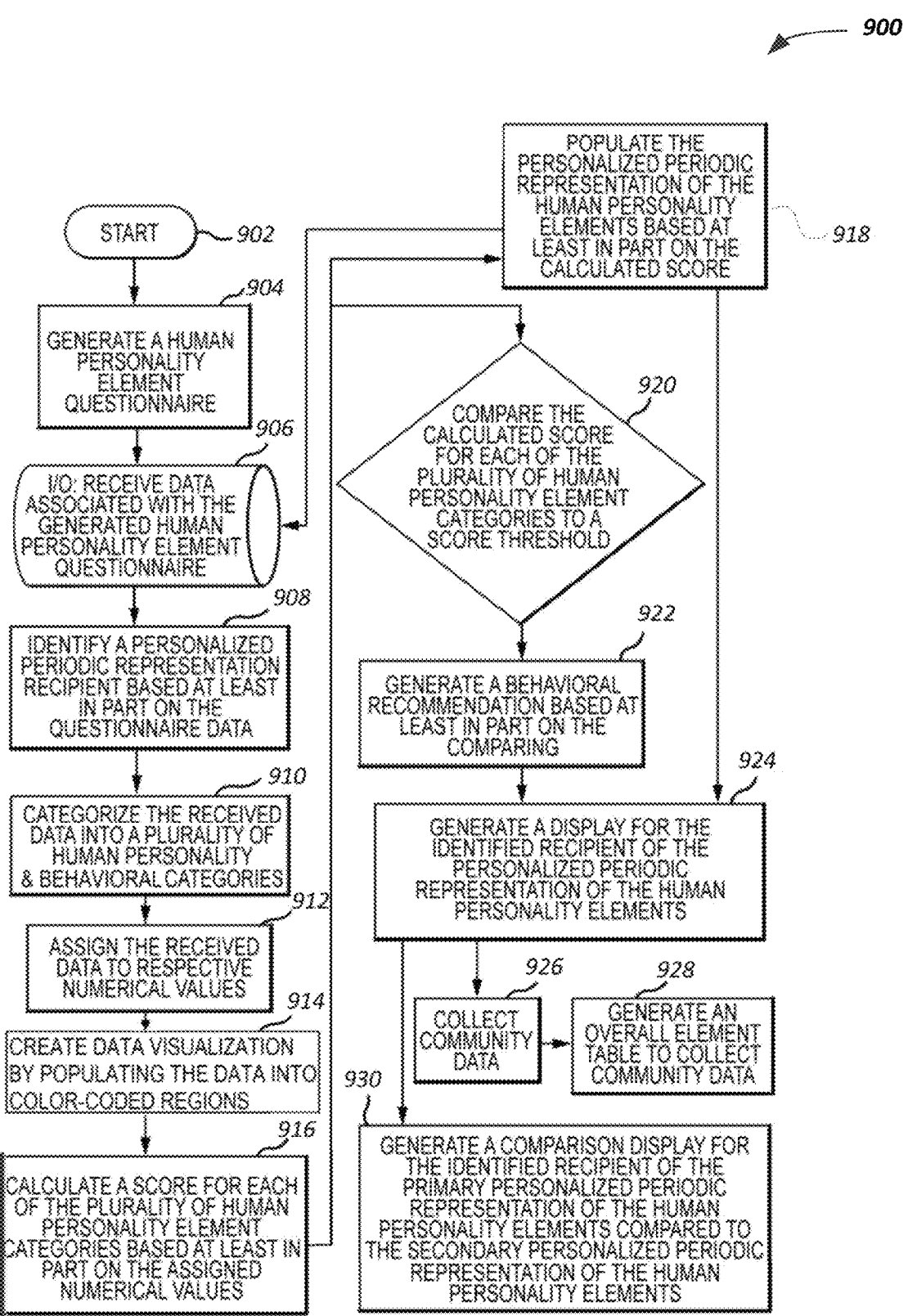

900

START — 902

904

GENERATE A HUMAN PERSONALITY ELEMENT QUESTIONNAIRE

906

I/O: RECEIVE DATA ASSOCIATED WITH THE GENERATED HUMAN PERSONALITY ELEMENT QUESTIONNAIRE

908

IDENTIFY A PERSONALIZED PERIODIC REPRESENTATION RECIPIENT BASED AT LEAST IN PART ON THE QUESTIONNAIRE DATA

910

CATEGORIZE THE RECEIVED DATA INTO A PLURALITY OF HUMAN PERSONALITY & BEHAVIORAL CATEGORIES

912

ASSIGN THE RECEIVED DATA TO RESPECTIVE NUMERICAL VALUES

914

CREATE DATA VISUALIZATION BY POPULATING THE DATA INTO COLOR-CODED REGIONS

916

CALCULATE A SCORE FOR EACH OF THE PLURALITY OF HUMAN PERSONALITY ELEMENT CATEGORIES BASED AT LEAST IN PART ON THE ASSIGNED NUMERICAL VALUES

918

POPULATE THE PERSONALIZED PERIODIC REPRESENTATION OF THE HUMAN PERSONALITY ELEMENTS BASED AT LEAST IN PART ON THE CALCULATED SCORE

920

COMPARE THE CALCULATED SCORE FOR EACH OF THE PLURALITY OF HUMAN PERSONALITY ELEMENT CATEGORIES TO A SCORE THRESHOLD

922

GENERATE A BEHAVIORAL RECOMMENDATION BASED AT LEAST IN PART ON THE COMPARING

924

GENERATE A DISPLAY FOR THE IDENTIFIED RECIPIENT OF THE PERSONALIZED PERIODIC REPRESENTATION OF THE HUMAN PERSONALITY ELEMENTS

926

COLLECT COMMUNITY DATA

928

GENERATE AN OVERALL ELEMENT TABLE TO COLLECT COMMUNITY DATA

930

GENERATE A COMPARISON DISPLAY FOR THE IDENTIFIED RECIPIENT OF THE PRIMARY PERSONALIZED PERIODIC REPRESENTATION OF THE HUMAN PERSONALITY ELEMENTS COMPARED TO THE SECONDARY PERSONALIZED PERIODIC REPRESENTATION OF THE HUMAN PERSONALITY ELEMENTS

FIG. 9A

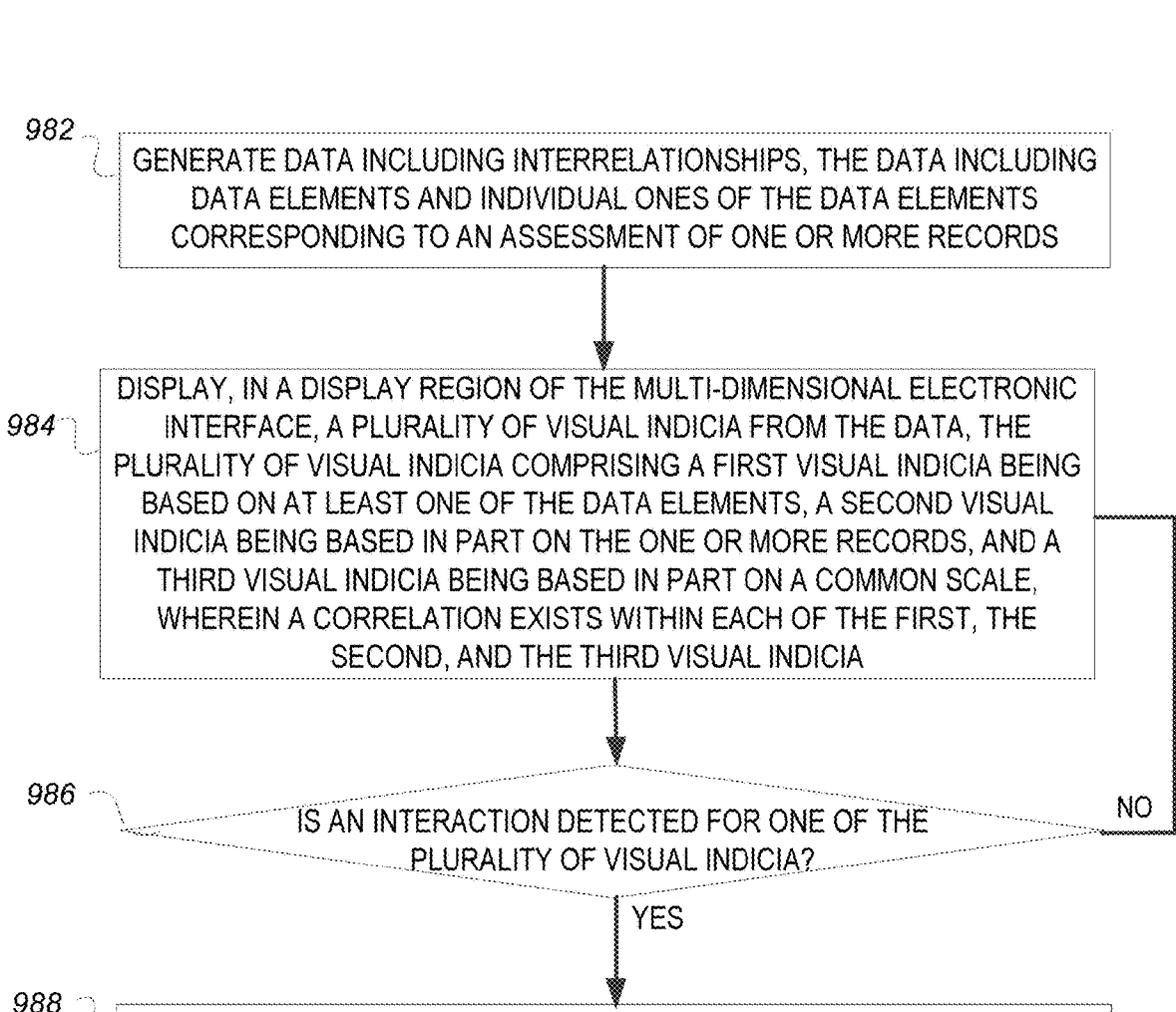

*980*

982 GENERATE DATA INCLUDING INTERRELATIONSHIPS, THE DATA INCLUDING DATA ELEMENTS AND INDIVIDUAL ONES OF THE DATA ELEMENTS CORRESPONDING TO AN ASSESSMENT OF ONE OR MORE RECORDS

984 DISPLAY, IN A DISPLAY REGION OF THE MULTI-DIMENSIONAL ELECTRONIC INTERFACE, A PLURALITY OF VISUAL INDICIA FROM THE DATA, THE PLURALITY OF VISUAL INDICIA COMPRISING A FIRST VISUAL INDICIA BEING BASED ON AT LEAST ONE OF THE DATA ELEMENTS, A SECOND VISUAL INDICIA BEING BASED IN PART ON THE ONE OR MORE RECORDS, AND A THIRD VISUAL INDICIA BEING BASED IN PART ON A COMMON SCALE, WHEREIN A CORRELATION EXISTS WITHIN EACH OF THE FIRST, THE SECOND, AND THE THIRD VISUAL INDICIA

986 IS AN INTERACTION DETECTED FOR ONE OF THE PLURALITY OF VISUAL INDICIA?          NO

YES

988 DISPLAY A GROUP OF VISUAL INDICIA, IN THE DISPLAY REGION, RESPONSIVE TO AN INTERACTION WITH ONE OF THE PLURALITY OF VISUAL INDICIA, WHEREIN THE PLURALITY OF VISUAL INDICIA POSITIONED ON THE MULTI-DIMENSIONAL ELECTRONIC INTERFACE IN A SIDE-BY-SIDE ARRANGEMENT TO PROVIDE COLLECTIVE ACCESS OF THE DATA WHILE THE GROUP OF VISUAL INDICIA IS PRESENTED WITH THE PLURALITY OF VISUAL INDICIA

*FIG. 9C*

NETWORK COMPONENTS
_1014_

MEMORY
_1004_

ORIENTATION ELEMENT
_1008_

POWER COMPONENTS
_1016_

PROCESSOR
_1002_

HEALTH ELEMENT
_1010_

INPUT ELEMENT
_1018_

INTERFACE ELEMENT
_1006_

IMAGING ELEMENT
_1012_

600

SYSTEM AND METHOD FOR IMPROVED DATA STRUCTURES AND RELATED INTERFACES

CROSS-REFERENCE TO RELATED APPLICATIONS

This application is a continuation of U.S. application Ser. No. 17/335,739 filed Jun. 1, 2021, which is a continuation of U.S. application Ser. No. 16/582,698 filed Sep. 25, 2019, now U.S. Pat. No. 11,049,299, which claims the benefit of U.S. provisional application Ser. No. 62/736,661 filed Sep. 26, 2018, the disclosures of which are hereby incorporated in their entirety by reference herein.

TECHNICAL FIELD

The present disclosure generally relates to interfaces and data structures for tracking emotional and behavioral traits, and in particular relates to improved graphic visualization of emotion and behavioral testing for individuals and entities using specific data provided by input methods, incorporating dynamic changes, and grouping together of traits by their correspondences and levels of each trait to reflect a flat three-dimensional assessment.

BACKGROUND

Personality and behavioral analysis programs provide individuals and entities with valuable insight into emotion and behavioral traits. In an example, Myers-Briggs Type Indicator® (MBTI®) provides technical assessments representing evaluation results for emotion and behavior of individual and entities. The technical assessments are useful to sort individuals into predetermined emotion type categories or to understand an entity's strength and composition. The emotion type categories for individuals, for example, are also indicative of behavioral proclivities. The MBTI® technical assessment testing makes research of psychological types and emotion accessible to any user. The MBTI® attempts to make sense of what one may otherwise recognize as random behavior. In this way, the random behavior is codified in a technical manner as a result of differences in ways people prefer to use their mental capacities. With MBTI®, a common technical thread is created and used as a reference point to bring together people of different mental capacities in a form of a connection. While this type of MBTI® technical assessment is useful for individual introspection, the MBTI® does not provide behavioral analysis or guidance for dynamic changes and also does not provide graphic visualization that incorporates correspondences between various input data provided to the generate the assessment. In another example, a DiSC® test provides a technical personal assessment tool that may be used to identify individuals' behavioral preferences and motivations in a workplace. These technical assessment results may promote awareness in workplace collaboration.

SUMMARY

An interactive system may include a multi-dimensional electronic interface; at least one processor; and memory comprising instructions that, when executed by the at least one processor to receive data elements corresponding to an assessment of one or more records; display a plurality of visual indicia derived the data, the plurality of visual indicia including interpersonal categories, each belonging to a group, and each identifying a level of impact, wherein the plurality of visual indicia are positioned in a side-by-side arrangement in each group to provide a collective view of the associated levels of impact.

A device may include a display; at least one processor; and memory comprising instructions that, when executed by the at least one processor cause the device to receive data on at least one participant; determine a score for each of a plurality of categories related to emotions and behaviors based on the received data; determine a correspondence between at least one category with at least one other category; and display a plurality color-coded regions including individual blocks representing the categories and identified by a specific color, each individual block having a fill level associated with the score of the respective category, and indicating the correspondence between the at least one category with the at least one other category.

A processor-implemented method may include displaying a first group of color-coded regions representing emotions and behaviors for data collected from one or more participants using an input method; determining correspondences within the first group of color-coded regions; providing individual ones of the first group of color-coded regions with a first portion of pixels in a first color associated with a value in the data based in part on the correspondences; providing a second portion of pixels in the individual ones of the first group of color-coded regions a second color associated with a neutral indication; determining changes to the data over discrete or random intervals of time, the changes modifying the correspondences; and dynamically changing the first portion of pixels and the second portion of pixels to update the display of the first group of color-coded regions.

BRIEF DESCRIPTION OF THE DRAWINGS

Some of the features and benefits of the present disclosure having been stated, others will become apparent as the description proceeds when taken in conjunction with the accompanying drawings, in which:

FIG. 3C illustrates one example aspect of a dynamic data structure that supports the dynamic interfaces for displaying the flat-three dimensional representation of traits or elements, in accordance with an embodiment of the disclosure.

FIGS. 9A, 9B, and 9C illustrate flowcharts of example methods to achieve the interfaces for the flat three-dimensional representation of traits or elements, in accordance with an embodiment of the disclosure.

Figure 1:
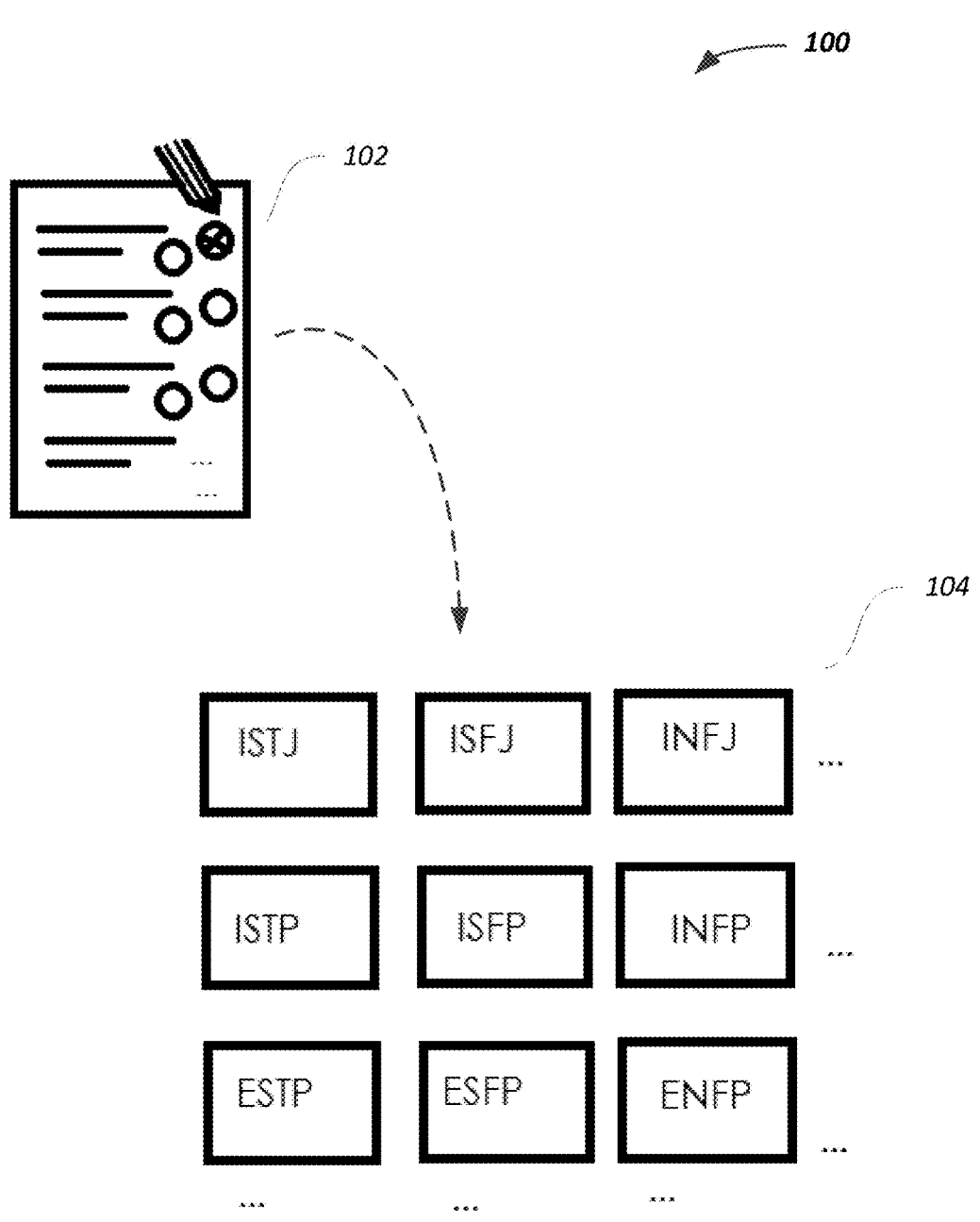
FIG. 1 is a schematic diagram of an emotion traits addressed in an example of the present method and system that may benefit from the improved interface and data structure presently disclosed, according to an embodiment.

While the disclosure will be described in connection with the certain embodiments, it will be understood that it is not intended to limit the disclosure to those embodiments. On the contrary, it is intended to cover all alternatives, modifications, and equivalents, as may be included within the spirit and scope of the disclosure as defined by the appended claims.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The method and system of the present disclosure will now be described more fully hereinafter with reference to the accompanying drawings in which embodiments are shown.

Herein disclosed are examples of an interactive system and a method for improving technological and graphic visualization of emotional and behavioral testing for individuals and entities using dynamic changes that include grouping together of traits by their correspondences and levels of each trait to reflect a flat three-dimensional assessment, and for improving data structures by incorporating using specific data provided by input methods. MBTI® represents a limited presentation of information that may be a mere reflection of the individual's or entity's static emotion type. Further, while the DiSC® test provides guidance of behavior modification in a limited number of dominant behavior types to help adapt individuals to behavioral needs of coworkers or teammates, this technical test may be limited in its applicability to personal self-awareness and growth, and is limited in its ability to respond to dynamic changes and in visualization of the assessment. Furthermore, an interface incorporating these test may not take into consideration limited interactive aspects in smaller devices, such as wearable devices.

The present system brings together research from a wide range of sources and ideas including positive psychology, dialectical therapy, cognitive behavioral therapy, mindfulness practices, health & wellness, emotional intelligence and problem-solving into a single visualization and instrument with a focus on holistic well-being. The system measures emotions and behaviors along with specific actions. This enables a holistic view of tools that aid in developing insight and coping strategies to aid in stronger mental health and well-being.

The visualization generated by the system have been shown to help the subject articulate what he or she may be feeling, which in turn has been shown to be important in reducing the feeling of negative emotions. Neuroscientific research has shown that articulating negative emotion helps to reduce the sensation of fight or flight on the amygdala. Furthermore, the system connects assessment and action (i.e., knowing and doing). Through the visualization we make the findings understandable, insightful, and actionable. The visualization helps a subject to identify what they are feeling and consider potential underlying reasons for the feelings.

The systems and tools disclosed herein helps individuals, professionals, organizations, etc., to understand all of the elements that make up one's personality and behavior. More importantly, the system allows everyday people to make connections between their behavior, feelings, and actions. By understanding all of the elements, the most salient elements that may be affecting the individual's well-being may be captured and identified. This may indicate how the individual fares with respect to that element, and how the individual may activate, or improve, that element using various combinations of elements. This may be accomplished by connecting the dots between the elements and providing a visualization that creates an integrated and holistic whole-being evaluation. This tool may be used by individual for personal or professional reasons, by corporation or employers, schools, doctors and medical professionals, etc. The tool may be one day available at retail establishments.

The system may include one or more processors and memory including instructions that, when executed in part by the one or more processors, cause the one or more processors to support or perform certain function is disclosed. In addition, a method using the system or any system configured in the manner as disclosed herein is also discussed. The technological and graphical visualization and the system of the embodiments disclosed herein provide a technical assessment that is easier to understand by pulling together research from a multitude of sources and by exploring positive psychology and the connection between mindset and behaviors and their impact on emotion and further action Furthermore, a non-transitory medium including instructions for executing on one or more processors is available to enable any system to support or perform the functions as follows.

The present disclosure provides software implementation on hardware to improve technological and graphic visualization of emotional and behavioral testing for individuals and entities. The software implementation may be by a computer-implemented method for generating a personalized grouping of individual elements or traits by determining correspondences in the traits and by determining levels of each trait that are altogether reflected in a flat three-dimensional assessment. For example, the flat three-dimensional assessment provides a grouping of traits as contributing to or being one of: an achievement measure; a sensibility measure; a communication measure; a measure of a doing and a being; a leadership measure; an emotional intelligence measure; a relationship measure; a learning measure; a guiding measure; or stressors measure. The individual traits, therefore, contribute to one dimension of the assessment, while the grouping provides a second dimension and a third dimension is provided by the levels in each trait. These present assessment is referred to as flat three-dimensional as the visualization is provided in a two-dimensional plane but incorporates at least three different features. Furthermore, the visualization is provided using colors to the grouping and using pixels of a first color and of a neutral color to provide the levels in each trait.

An example device incorporating the system and method of the present disclosure includes a display, at least one processor, and memory comprising instructions that, when executed by the at least one processor cause the device to perform functions for improving visualization of assessments in a graphical participant interface. For example, the improvements are by displaying a first group of color-coded regions representing emotions and behaviors for data collected from one or more participants using an input method. The first group may represent the above-referenced grouping of traits, also referred to herein as elements. The first group then includes many color-coded regions of different colors according to the grouping. Correspondences are determined within the first group of color-coded regions. In an example, a formula that incorporates a summation of the grouping of the traits in an averaging function within each group and that incorporates a subtraction of the stressors measures may be used to determine the correspondences. This provides the first and second dimensions previously discussed.

The device instructions also cause the device to provide individual ones of the first group of color-coded regions with a first portion of pixels in a first color associated with a value in the data based in part on the correspondences. In a similar manner the device is caused to provide a second portion of pixels in the individual ones of the first group of color-coded regions a second color associated with a neutral indication. This provides a visualization of the three dimensions in a flat two-dimensional plane without sacrificing information. Furthermore changes determined to the data over discrete or random intervals of time may then modify the correspondences to dynamically change the first portion of pixels and the second portion of pixels, which updates the display of the first group of color-coded regions. The display may reflect certain levels associated with each category of element by adjusting the "fill level" of a category. This may indicate a certain level of satisfaction with respect to that particular category. These categories may include stressors and non-stressors. The stressors may have an effect on the non-stressors and a high level stressor may tend to lead to a lower level non-stressor.

In another example, the present method and system improves on visualization of assessments and changes the visualization dynamically, but also improves data structures by incorporating specific data provided by input methods. For example, the method can include generating, by a processing system, an emotion element questionnaire as the input method. Then at least one processor communicates with a multi-dimensional electronic interface to generate data including interrelationships. The data includes data elements that each corresponds to an assessment of one or more records. For example, the data may correspond to each of the above-referenced traits. A display region is provided for the multi-dimensional electronic interface. A number of visual indicia from the data are displayed in the display region with the visual indicia including a first visual indicia corresponding to a first data element of a first assessment based on the one or more records. A group of visual indicia is displayed in the display region in response to an interaction with the first visual indicia. Further, a second visual indicia is displayed corresponding to a second data element of a second assessment based on the one or more records, where the second data element shares a first correlation with the first data element. A third visual indicia is displayed corresponding to a third data element of a third assessment based on the one or more records, where the third data element shares a second correlation with the first data element. Still further, a fourth visual indicia is displayed corresponding to a fourth data element of a fourth assessment based on the one or more records, where the fourth data element shares a third correlation with the first data element. The first, the second, the third, and the fourth data elements have a common scale to provide a common measure of deviation, if any. The first visual indicia, the second visual indicia, the third visual indicia, and the fourth visual indicia are positioned on the display device in a side-by-side arrangement to provide collective access of the data.

The above features present accuracy of an emotion assessment by providing visualization not previously available. Such visualization also captures dynamic changes in traits that are independent and also by grouping traits together using color-coded regions and pixels variations. Particularly, as individual traits have relationships to other traits or elements, and as the individual traits or elements have group based relationships, there is a significant benefit from visualization of these relationships in the individual aspects, as well as the grouping, to individual levels (pixels assigned colors for the trait and a neutral color that are subject to dynamic changes, for example). In addition, as the input from participants in a test may change as certain traits or elements are not completely objective, it is beneficial to capture these in discrete and/or random time intervals. These changes reflect more of emotional and behavioral aspects to the emotion. As such, another benefit offered in the present method and system is the ability to visualize dynamic changes by providing the ability to update the visualization in the three dimensions to reflect these dynamic changes. The static nature of prior implementations relied on an input-for-output association that generalized emotion in an expected manner. This is also erroneous as an assessor of the output of the static system then relies on improper or inaccurate and dated information to form a decision. In using the present system and method, an assessor is able to recognize that color-coded regions have changed because of the first pixels taking on lesser of an assigned color to the group and taking on more of a neutral color indicating that dynamic changes have occurred. In addition, as the interface is color-coded, grouped, and includes pixel assignments, there is no delays or latencies of a computer implementation. This reflects an efficient use of interface with participants and an efficient use of data by overwriting prior data to provide efficient memory management as well. These benefits allow the present system and method to be implemented on wearable devices, for instance, because wearable devices are limited by small screen size and limited memory capacity.

Other aspects and features of the present disclosure will become apparent to those of ordinary skill in the art after reading the detailed description herein and the accompanying figures.

The present disclosure is at least directed to software implementation on hardware to improve technological and graphic visualization of emotional and behavioral testing for individuals and entities. The software implementation may be by a computer-implemented method for generating personalized categories or grouping of individual elements or traits by determining correspondences in the traits and by determining levels of each trait that are altogether reflected in a flat three-dimensional assessment. In addition, the software implementation allows usage of emotional and behavioral testing in devices with limited display space and limited memory capacity. In an example, an assessment or result of the emotional and behavioral testing in the present interactive process displays the flat three-dimensional representation of traits in a periodic-style table.

The technological findings and visualization herein may help a subject articulate what otherwise may be described as feelings which has been shown to be important in reducing negative emotions. Neuroscientific research supports that articulating negative emotion helps to reduce the sensation of fight or flight on the amygdala part of the cerebral hemisphere. The technological and graphical visualization helps to identify what individuals may be feeling and consider potential underlying reasons for the feelings. A benefit of implementing the present system and method is that the technological visualization features herein provide a connection between assessment and action. As "knowing" and "doing" are two different things, the present system and method offers advantages over prior technology by converting findings into visualization for understandable, insightful, and actionable items.

FIG. 1 is a schematic diagram 100 of emotion traits addressed in an example of the present method and system that may benefit from the improved interface and data structure presently disclosed, according to an embodiment. The schematic of FIG. 1 may be a MBTI® or DiSC® type test process 102 and result or assessment 104. Particularly, FIG. 1 illustrates a static process of securing answers to questions in the test process 102 that may be in a binary answer or multiple-answer format, and then determining a proper category for categorizing answers to those questions resulting in a determination of descriptors from predetermined descriptors. Furthermore, the descriptors may be combined to generate categories. For example, descriptors that may be available include extraversion (E), introversion (I), sensing (S), intuition (N), thinking (T), feeling (F), judging (J), and perceiving (P). As such, the short codes of ISTJ, ISFJ, INFJ, ISTP, ISFP, INFP, ESTP, ESFP, ENFP, etc., are a combination of descriptors for the category in the result or assessment 104. As such, the process represents a static, dated, and non-scalable process for emotion assessment. Such a process also does not sufficiently engage a participant over time and is difficult to comprehend in small devices.

Figure 2:
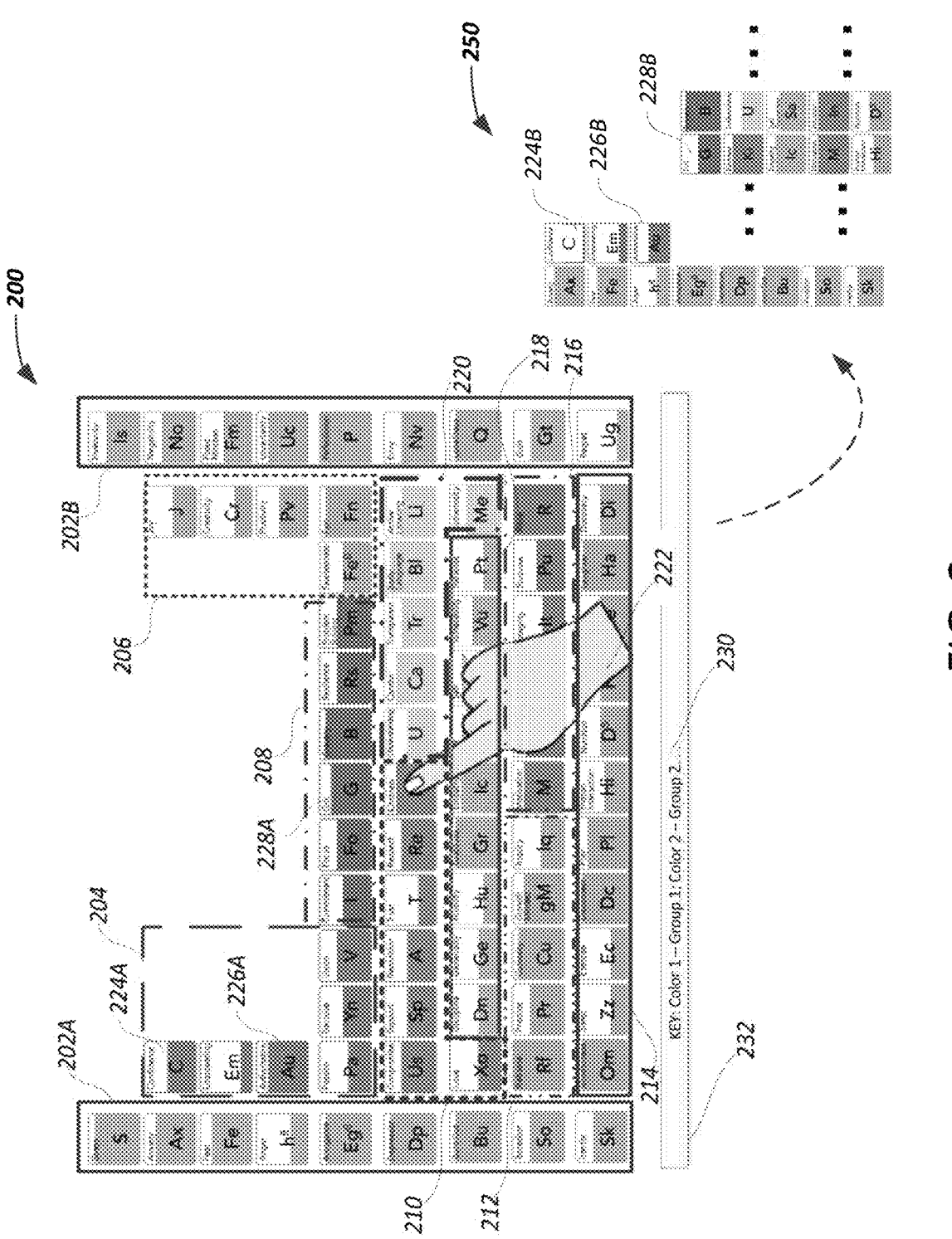
FIG. 2 illustrates an interface of the flat three-dimensional representation of traits or elements, and dynamic changes in process, in accordance with aspects of an embodiment of the disclosure.

FIG. 2 illustrates an interface 200 of a flat three-dimensional representation of traits or elements, and dynamic changes 250 in process, in accordance with aspects of the disclosure. Based at least in part on a questionnaire provided in a software interface, such as a multidimensional electronic interface, answers are received to the questionnaire data. The answers represent data including interrelationships because some questions are provided with relation or reference to other questions in the questionnaire and these relations or references are stored. The data is then analyzed to generate a personalized visual representation for a participant or an entity depending on the situation. Such a visual representation is provided in the form of a table 200 with groupings 202A, B-220 using unique colors to each group. In an example, a participant may be identified with particularity, while other embodiments may strip identity from the data and maintain other generic identifiers. The generic identifiers include demographic factors, age, occupation and other features determined as essential to the emotion test. In another example, more than one participant may be identified where a company and an employee are each identified as participants to generate the personalized visual representation of their relationship. This process advances privacy in data transfer and storage processes, and resolves an issue advanced in computer technology of how to transfer digital data in a manner that does not infringe on participant's expectation of privacy. This enhances participation in a system of testing as disclosed herein.

In FIG. 2, the table may represent a known relationship table for ease of use or recognition purposes to the participant. In an example, a chemical periodic table is used, where each trait or element is provided in its own region of a display region. In the table of interface 200, groups may be provided with some form of symmetry or unison to enable ease of identification and to enable easy assignment of colors to the groups. For example, even though shown as different shades of colors, groups or groupings 202A, 202B-220 represents unique colors in each group. As such, the different traits or elements (or categories) are displayed as part of a unique group. In an example implementation, the groups may be edits by a participant or by a supervisor of the system to change specific traits or elements. In a further example, the participant or supervisor needs to provide authentication request and secure allowance to be able to implement such an edit to the group or groupings 202A, 202B-220. As such the table of interface 200 is a display of a first group of color-coded regions representing emotions and behaviors for data collected from one or more participants using an input method, such as the questionnaire.

The color-coded regions in table 200 represent various traits or elements, numerical values for which are determined from answers to the questionnaire. The questionnaire is a multi-answer questionnaire to allow a range of answers (fuzzy) to each question. The numerical values, therefore, represent a range of values for each of the traits or elements. Further, the interface 200 element identifiers for each of the interpersonal elements or traits marked within each respective color-coded region. For example identifier S represents an element or trait of stress, while identifier Ax represents an element or trait of stress anxiety. Fe represents fear, C represents confidence, Em represents empowering, G represents grit, Au represents authoritative, etc. The color-coded regions are grouped into what may be an emotion or behavior for an individual or entity comprising the traits or elements of those color-coded regions.

In an example, an individual or entity with a personalized visual representation, such as table 200, displaying high values for Confidence, Empowering, Authoritative, Passion, Decisive, and Vision, may be described as having an emotion or behavior identified in that group 204. Group 204 may be assigned to a Leadership emotion or behavior. The assignment may be predetermined, but the allocation of the traits or elements to the group may be changed as previously described. In addition, level of participation in each group is dependent on the answers to the questions provided and may change dynamically based on answers to other questions of a questionnaire in a subsequent test administered randomly or at discrete time intervals. Group 202 (including non-contiguous groups 202A and 202B) is a group formed of Stressors elements or traits, such as Is (Insecurity), Negativity (No), Fixed Mindset (Fm), Perfectionism (P), Anxiety (Ax), Burn Out (Bu), etc. Group 206 is a group for Sensibility traits or elements. Group 208 is a group for Achievement traits or elements. Group 210 is a group for Relationship traits or elements. Group 212 is a group for Learning traits or elements. Group 214 is a group for Doing & Being traits or elements. Group 216 is a group for Guiding traits or elements. Group 218 is a group for Emotional Intelligence traits or elements. Group 220 is a group for Communication traits or elements.

Also illustrated in FIG. 2 is the use of different number of pixels of colors. Even though FIG. 2 is show in shades of grey, a person of ordinary skill, upon reading the present disclosure, would understand that the description herein is supporting colors and not limited to the greyscale used for illustrative purposes only. The different number of pixels of colors is generated by formatting the table of interface 200 to include a fixed aspect ratio for the table and a second fixed aspect ratio for each color-coded region in the first group of color-coded regions. For example, the table in interface 200 provides multiple elements or traits (S, Ax, C, Fe, Em, Is, J, No, Cr, Fm, etc.) with specific pixels of color, such as in reference numerals 224A and 226A is of a same group 204, and may be of color-coded regions that are each provided with a mix of blue color pixels and neutral color pixels. In an example, the neutral color pixels may be white, black, grey, or may be customizable to a background color available in the interface 200. Further, reference numeral 228A, being in a different group, i.e., group 208, may be a color-coded region of a mix of red color pixels and the neutral color, for instance.

The table 200 may also be seen as providing data including correspondences or interrelationships between the elements or traits by having them grouped together, for instance. Furthermore, aside from the grouping, additional correspondences or interrelationships may be identified using impact analysis as subsequently described. Particularly, the data providing the data elements in each of groups 202A, 202B-220, each correspond to an assessment of one or more records from the results provided in response to one or more questionnaires. For example, an emotional and/or behavioral element questionnaire is generated to include questions associated with one or more categories of individual emotional and/or behavioral elements. In one instance, the questions may be indicative of the identified emotional and/or behavioral elements belonging to categories or groups previously described, including: Relationship, Communications, Energy, Achievement, Mindset, Guiding, Emotional Awareness, Self Care, Stressors. These groups are discussed in further detail with respect to FIG. 12 below. In another instance, fewer, additional, or alternate categories or groups may be included to encompass various questions and their corresponding elements or traits. As such, the data from the answers may be categorized, by the processing system, into a number of descriptors or individual emotion elements (e.g., reference numerals 224A, 226A, and 228A), which may further be categorized in their respective groups or groupings 202A, 202B-220.

An assignment process of the present system and method assigns the data to respective numerical values. For example, these numerical values may be absolute or relative. When the numerical values are relative, a common scale may be used to reference the numerical values. For example, each answer may be assigned a respective numerical value, in some embodiments in a range of 1-5. As such a common scale is established. When the numerical values are absolute, then they may be classified by language in the responses—e.g., by providing scores or values to specific words. An average numerical value of the questions within each emotion and behavioral category may then be calculated. For example, in a questionnaire of 100 different questions, if question numbers 2, 16, 28, 62, and 63 relate to the communication category of the identified emotion elements or traits, the average numerical value of the answers provided to these questions may be calculated. Similar average numerical values may be calculated for each of the other categories or groups. The numerical values of each category or group may then be added together. In an example, the average numerical value for each question associated with a category or group, such as the stressors category or group, may be separately calculated and multiplied by a predetermined numerical factor. For instance, using a predetermined numerical factor of 2.5 graduates the stressors impact to elements within the group and across groups.

The calculation process advanced in the present system and method provides a score for each of the elements or traits in each of the groups or categories based at least in part on the assigned respective numerical values previously determined. For example, the stressors impact value may be subtracted from calculations in other categories and groups (summed elements or traits in each of the other categories and groups providing a starting value) in order to compute an overall score. The score may be indicative of a degree to which the stressors category questions are impacting the remaining categories of emotion and behavioral elements. As such, the layout of the table in interface 200 as well as the number of pixel of assigned color, which may represent an amount of effect of each element or trait in the category or group and across categories and groups, bears significance for providing indication of how much certain groups weigh on a final emotion test of an individual or entity. The impact provides correspondences or interrelationships between each element or trait in a category or group, as well as provides correspondences or interrelationships between categories and groups. For this reason, the data generated from the answers have existing or implicit interrelationships that are explicitly defined by the above numerical values and subsequent calculations.

In addition to the above, the interface 200 is dynamic and discrete or random changes provided from participants are considered at the time provided (or at a predetermined time) to effect changes to the number of pixel of assigned color (versus, for e.g., a neutral color). Such a process effectively tracks and displays information intended for the reviewer in a manner that enables the reviewer to better comprehend the test. In addition, the color-coded regions for each element or trait, as well as the number of pixels assigned to colors in each of the color-coded regions helps accurately determine the present state of a participant's emotion assessment. This process is particularly useful in devices with limited memory space—to efficiently manage data updates by overwriting the data, which is relied upon for the above-referenced assignment of numerical value and subsequent calculations of the score. Furthermore, this process is also useful for efficiently managing display regions in displays of smaller devices, because of the use of groupings of the color-coded regions and because of the use of assigned number of pixels in the manner described. Here, more information is provided by the flat three-dimensional displays and more information is presented accurately and in an updated manner than in prior static systems and methods. A key 230 may be displayed with associations to the individual colors in the first color-coded regions in an area 232 of the display offset from the first color-coded regions of the table in interface 200.

An example of an interface update is provided via partial interface 250 which illustrates a table update to the table in interface 200. In the example partial interface 250, which is an excerpt displaying updates to the table of interface 200, certain elements or traits have undergone an update in view of new input received from an individual or entity to which the table in interface 200 belongs. In the example partial interface 250, elements 224B, 226B, and 228B are illustrated with additional or fewer pixels of assigned color than in the prior table in interface 200 to reflect a dynamic change associated with inputs received from a participant or entity at random and/or discrete time intervals. The additional or fewer pixels, therefore, represent overlapping pixels as some of the pixels may have a first color and others may have a second color, but that these pixels may be changed to reflect fewer of the first color and more of the second color. As illustrated, in 224B confidence is an element that has substantially changed in measure and has fewer assigned pixels than from the previous element 224A in the previous table 200. As such, participant or entity has indicated a change in their responses that reflect the change in the confidence and may also provide further information as to emotion of the participant or entity. In an example, the participant or entity, or other authorized person, may review the entries by selecting any one of the elements using a pointer, a touch interface, or other interactive mechanism 222. When selected, the current status of the element and/or the current status of the group may be provided in an overlay or in a different interface as further described in FIGS. 3A-7.

FIG. 2 also illustrates visual indicia as in the elements and groupings from the data in the interface 200. The visual indicia includes data elements, or categories (specifically labeled in FIGS. 12 and 13), from different assessment based on the one or more records and based on a common scale as previously discussed. The numerical values assigned, along with the calculation previously described, support the generation of the visual indicia by requiring certain number of pixels in color-coded regions (representing the elements or traits) to be of a color assigned to a group to which the color-coded regions belong. The remaining portions of the color-coded regions that are not assigned a color are provided with default or neutral colors. A correlation exists within at least two data elements of the data elements. In an example, the above discussion of the impact between elements provides one such correlation.

A benefit offered in the interface 200 of FIG. 2 is that the complete emotion information is available in a single interface, which represents collective access to the data from a participant or entity. Merely providing results in a display or a chart is limiting as the participant or entity requires browsing through multiple interfaces to be able to secure the results or assessments and to be able to review the substantive contributing elements in further detail. As such, the present system and method improves a participant interface to provide collective access via the interface 200 with selectable color-coded regions corresponding to the elements or traits, and with information offered in the grouping and in the pixels assigned to color codes under the grouping.

FIG. 2 then displays the visual indicia positioned on the multi-dimensional electronic interface in a side-by-side arrangement to provide collective access of the data. The group of visual indicia (as described at least in FIG. 3B) is presented with the plurality of visual indicia as in the color-coded regions of interface 200. The side-by-side arrangement includes non-continuous rows and columns formatted as a table in the manner of FIG. 2. A first, second, third, and fourth data elements in the data elements of FIG. 2 may include a preselected set of traits and behaviors as illustrated in the interface 20. In an instance, the first data element may correspond to a trait, while the second data element, the third data element, and the fourth data element may be arranged with correspondence to behaviors that impact the first data element.

Figure 3A:
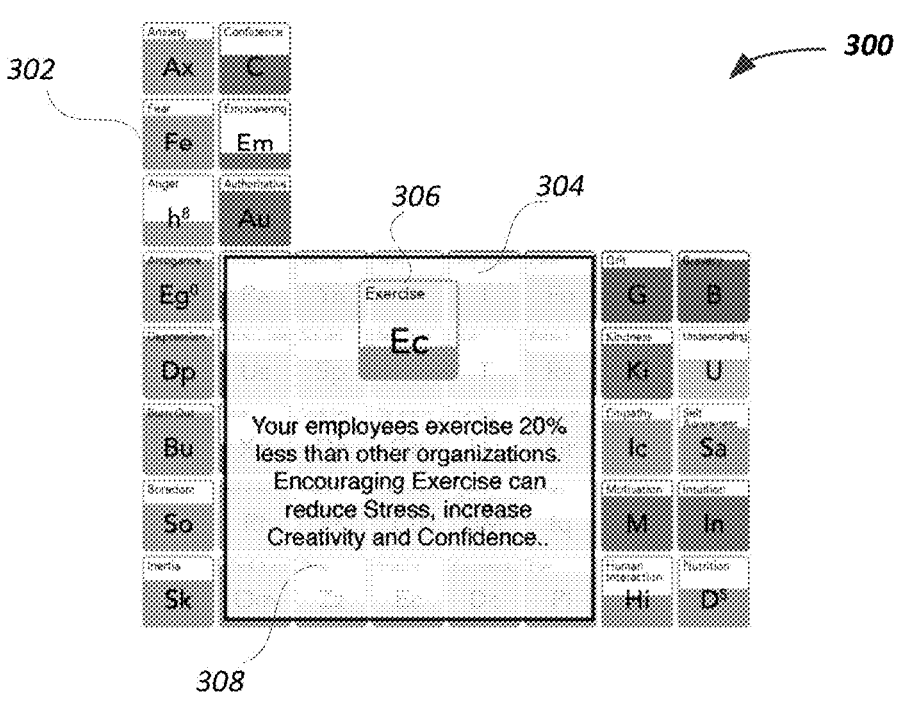
FIGS. 3A, 3B illustrate aspects of an example interface for representation of traits or elements and related information, in accordance with aspects of an embodiment of the disclosure.
Figure 3B:
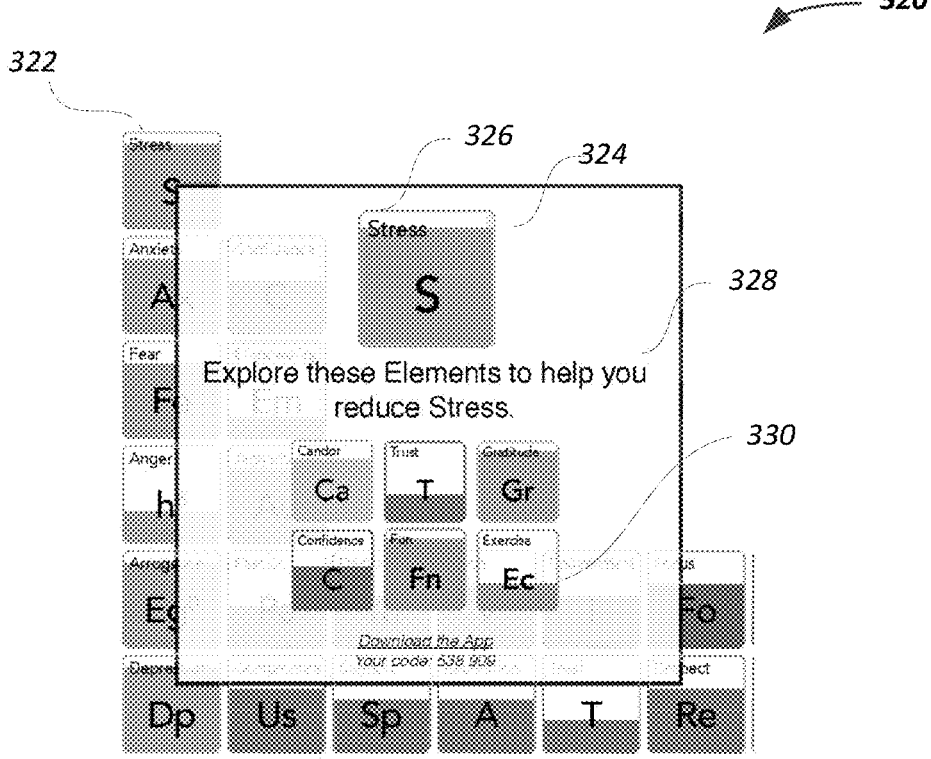

FIGS. 3A, 3B illustrate aspects of an example interface 300, 320 for representation of traits or elements, in accordance with aspects of the disclosure. In FIG. 3A, an example of the selectable color-coded regions described with respect to FIG. 2 is further detailed. An element Ec may be selected from a first group of color-coded regions 302 (representing a first group of elements or traits) provided in FIG. 2. Information 306, 308 as to the selected element Ec is then offered in an overlay 304 over the first group of color-coded regions 302.

In addition, the information 306 may retain the pixel colors from the selected element of the first group of color-coded regions, FIG. 3B illustrates displaying a group of visual indicia 330 from the table of interface 200 in the display region of the multi-dimensional electronic interface. The group of visual indicia 330 is displayed in an overlay 324 with additional information 328 to at least a selected element or trait (e.g., Stress 326, in the example of FIG. 3B). The correspondences or interrelationships to the Stress element or trait 326 are provided in the overlay (e.g., Candor Ca, Trust T, Gratitude Gr, Confidence C, Fun Fn, and Exercise Ec.). The amount of pixels indicating level of impact (e.g., correspondence or interrelationship) of each of these elements may be replicated from FIG. 2, but may also be dynamically changed to reflect specific relationships with the selected element 326. Particularly, the group of visual indicia 330 is a second group of color-coded regions that either maintain their initial correspondence or interrelationship from the global set of the table in interface 200 or may be changed to reflect new correspondence or interrelationship values that are within the global set, but are lesser because the other elements or traits are now removed and have no impact in the second group of color-coded regions or group of visual indicia 330.

Furthermore, currently responses may be shared with the individual participant of the technological testing assessment. However, the system and method herein also may be capable of functioning as part of an inter-connected technological workshop, where a team presents the findings by grouping them together to show the group as a collective. This makes the group aware that they are each experiencing similar emotions and to highlight what emotions and behaviors are at play for them which may be impacting the group dynamic. In a further aspect, the more data that is provided into the system, the better the accuracy of the determined individual scores because the determined individual scores are in relation to aggregate data.

The multi-dimensional electronic interface supports a dynamic graphical layout as exemplified in interfaces 200, 250, 300, 320. The multi-dimensional electronic interface is multi-dimensional for at least supporting assessments that provide information in two dimensions and that are required to represent the data presently part of the emotion testing. A third dimension is presented in the amount of pixels for each of the color-coded regions, which is also supported in the multi-dimensional electronic interface. The multi-dimensional electronic interface may also receive input if it is touch interface or includes software and hardware support for interactive features, including by a mouse or other type of pointer device. When a responsive to an interaction with one of the plurality of visual indicia, a group of visual indicia as discussed with respect to FIG. 3B is provided. As such, the present method and system support a display of the visual indicia of interface 200, positioned on the multidimensional electronic interface in a side-by-side arrangement to provide collective access of the data, along with the group of visual indicia of interface 320, presented in an overlay or other such method to retain context. FIG. 3B also illustrates that the overlay 324 has at least one of the second group of color-coded regions in an overlay over the first group of color-coded regions of interface 200 so that an edge of the overlay overlaps at least one color-coded region 322 of the first group of color coded regions of interface 320.

In a further implementation, the present disclosure is to a dynamic data structure 350 for supporting the dynamic interfaces described in FIGS. 2-3B. In an aspect, the dynamic data structure 352 includes nested tables 354-358, where the nested tables may share a key. For instance—the key may be at least one common element, such as the Description from Table 352. As such, the Description becomes a primary key, but additional keys may exist—like Position, for instance. In an example, the Position (or part thereof) may provide additional reference for a secondary key. Then a combination of the Description and the Element Score of the Position may be used to mine for the element score associated with the element of Table 352, from table 356. In addition, each table 352, 354, 356, and 358 provide information for the visual indicia in some way.

In an example implementation, a first table 352 provides the information for the element (e.g., element, color, title, position, description etc.), which is relevant to the first visual indicia (i.e., the cell or element in the table display of FIGS. 2-3B. A second table 354, 356 may be provided with a primary key 360, 362 from the first table 352. The primary key provides identification of correlated elements forming a group, for instance. In an example, the Description is useful to identify relationships via tables 354 and 358. For example, based at least in part on input received to questions posed to an individual or a group, the results may be correlated and provided as a relation from one element to every other element for the individual or a group. Such a relationship is provided in Table 358, which references each element against every other element. The relationship includes Improvement suggestions and may include an Improvement Element Score. The Improvement Element Score may be a value from 1-5 or a limited scale that may affect the element score, which in turn determines the level of color in each element. For example, when there is a weak relation between two elements, a participant response maintains this weak relation; then the Improvement Element Score for the two elements remains unchanged. As a result, the Element Score is unaffected in Table 352 from a default value, for example. As a result, a dynamic interface providing levels of color for the associated element displays a level of color that remains unchanged. As such, the information provided from tables 354 and 358 are relevant to the second visual indicia (the grouping of the cells or elements).

In an example, the nested tables 350 is particularly designed to use position information partly keyed to other tables in the nested tables allows for faster response to dynamic changes occurring at the lowest level tables. As the lowest level tables (e.g., tables 354, 356, and 358) include far lesser information, they load faster and are able to accommodate dynamic changes better. The specific dynamic structure of the nested tables 350, therefore, introduces a novelty in dynamic storage and processing of information.

Furthermore, nested table 350 includes a Position/Level key which relates to the position of an associated Element in the table. As element S is the first element in the table, it is positioned at a default reference to (0, 0) on an (x, y) axis of a display. The display, however, would be able to associate (0, 0) to a well centered interface by seeking a final x value and final y value from table 352. An averaging process then provides center x and center y coordinates that may be used to position the first element. The subsequent elements are referenced off of the first element; e.g., element Ax is provided position and level (0, −1, Element Score+/−Improv.), which means it is located in a cell on the same x axis as element S (i.e., x axis 0), but properly below element S (y axis −1), and with a level of color (e.g., 8+2 of color #FFFF00) provided by the Element Score 8+2, and with title S Stress. As illustrated in interface 200, this is shown as a full colored cell Ax below cell S. A third table 354, 356 (depending on which was previously referenced as the second table) may also share the primary key with the first table. The third table 356, for instance, provides numerical value, element score, etc., which may be relevant to the to the third visual indicia (e.g., the coloring level to be provided based on the value and/or scoring).

A fourth table 358 may provide related elements to focus on for Improvements to emotion and behavior that is relevant to the fourth visual indicia (e.g., the overlay information to suggest exercises to the participant for a selected element). An associated Improvement Element Score in the table is provided dynamically to affect to the Element Score of table 352 based at least in part on the responses provided by a participant that affects the interaction between elements in the table 358. Furthermore, the Element Value from table 356 may be associated with numerical values assigned from the answers to questions provided from a questionnaire. The Element Score may represent a fraction of the Element Value so as to support a common scale for display purposes.

An interactive device is, therefore, disclosed to use the above disclose novel dynamic data structure. The interactive device includes a multi-dimensional electronic interface, at least one processor; and memory comprising instructions that, when executed by the at least one processor cause the interactive device to perform functions for creating and maintaining the dynamic data structure. A first table is created by a function. The first table includes a first number of columns providing information for an element to define a location and a level of color associated with a section of a dynamic interface. A second table is created with a primary key from the first table and having a second number of columns less than the first number of columns for updating of contained information by the at least one processor at a threshold processor speed. In an example, as previously mentioned, a number of columns is selected for the tables 350 is to allow for dynamic efficiency the second table providing identification of correlated elements for the element.

A third table is created for sharing the primary key with the first table and for providing scoring requiring for the updating of the contained information in the second table. The scoring may be associated with dynamic input received from participants using the dynamic interface. A fourth table provides the correlated elements and associated improvement scores to support the updating of the contained information in the second table and provides additional information associated with improving emotion and behavior based in part on the scoring.

In a further aspect, the instructions that, when executed by the at least one processor further cause the interactive device to include a color code, a title, and a position to support the location for at least a first visual indicia of the dynamic interface. A further function from the at least one processor is to form a group associated with a second visual indicia. The group provides a variation, for other elements than the element, from a color code assigned to the element. The interactive device includes a numerical value to affect the scoring for third visual indicia. The third visual indicia reflect a level of color of the color code to be provided that is different from a default level of color. Finally, information may be provided for improving the emotion and the behavior based in part on the scoring. The information may be in the form of fourth visual indicia to overlay any data in the dynamic interface.

Figure 4:
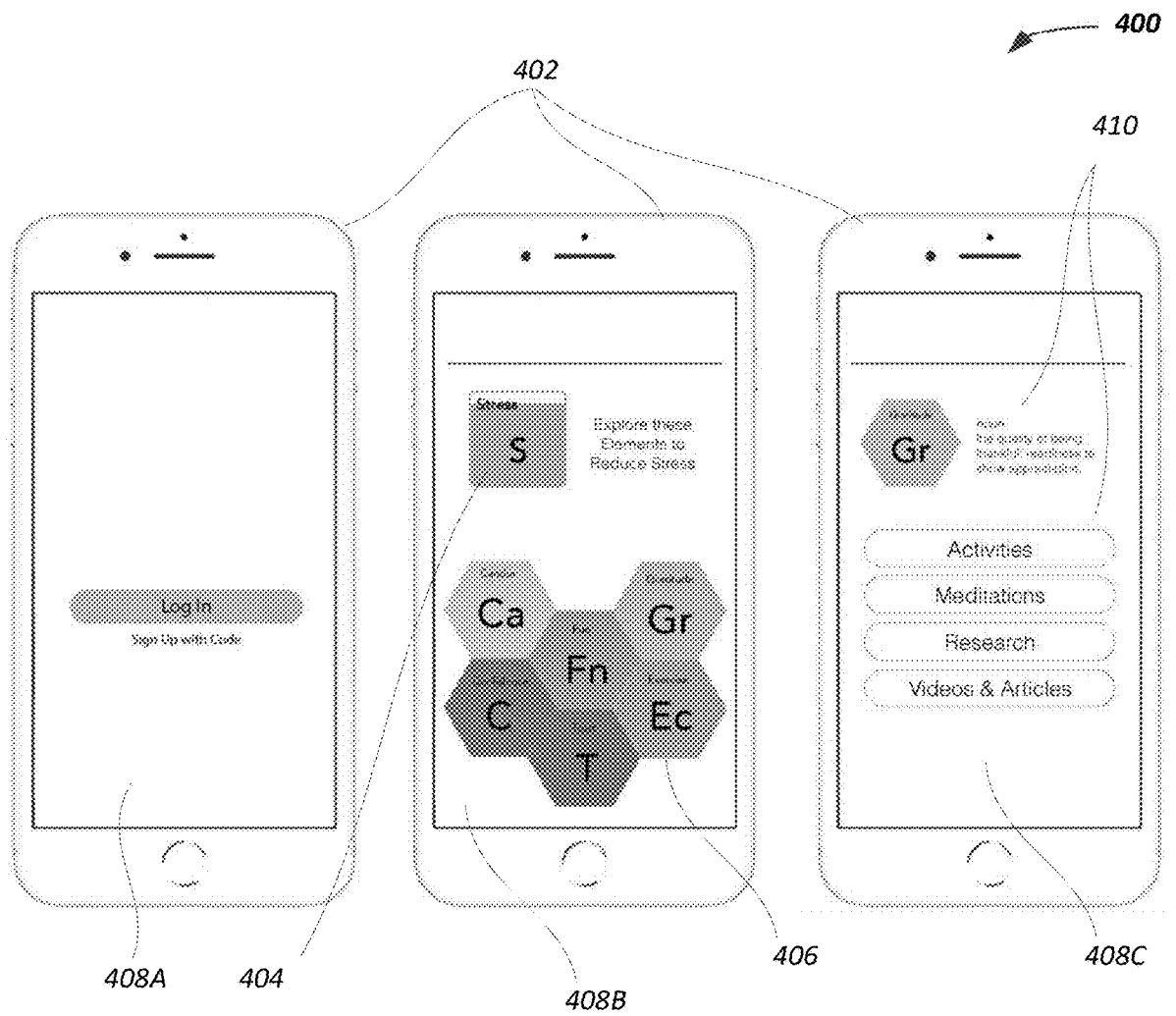
FIG. 4 illustrates one example portion of interfaces for displaying the flat three-dimensional representation of traits or elements in mobile devices, in accordance with an embodiment of the disclosure.
Figure 5:
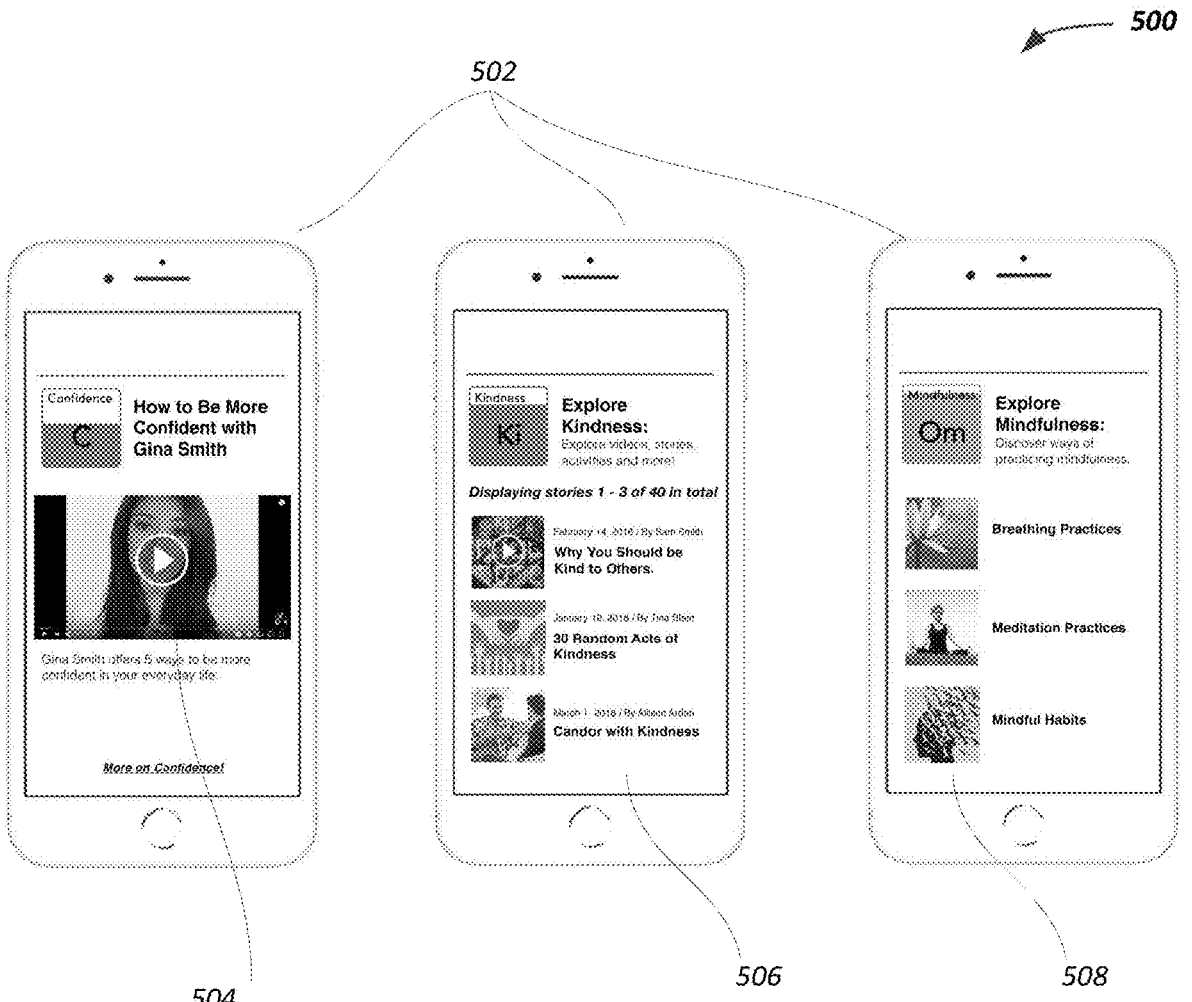
FIGS. 5 and 6 illustrate example portions of interfaces for displaying the flat three-dimensional representation of traits or elements in mobile devices, in accordance with an embodiment of the disclosure.
Figure 6:
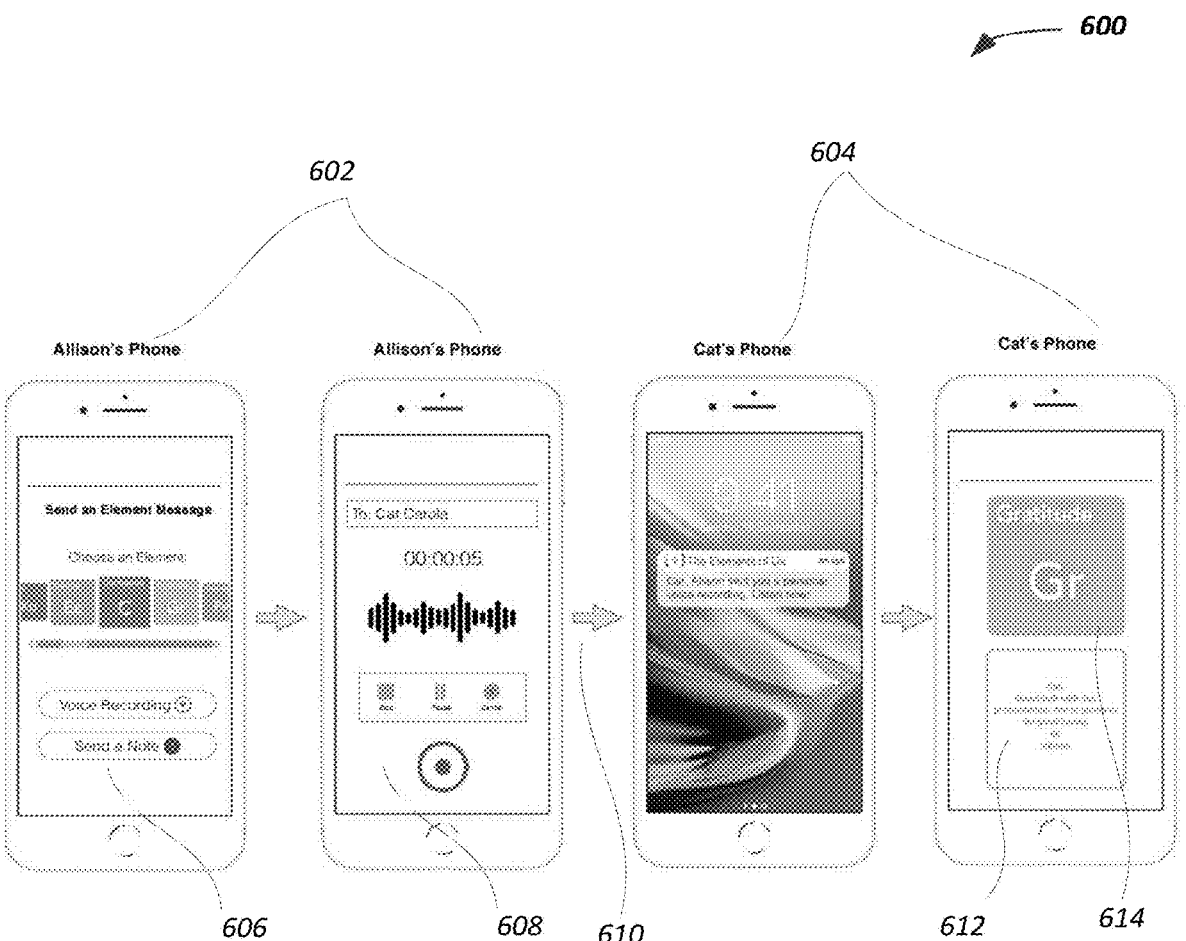

FIGS. 4, 5, and 6 illustrates one example portion of interfaces 408A, 408B, and 408C for displaying the flat three-dimensional representation of traits or elements in mobile devices 402. As in the case of FIG. 3B, interface 408B is provided after authenticating a participant using the present system and method on a mobile device 402 via interface 408A. In such an example process, the software enabling interfaces 408A, 408B, and 408C may support provisioning of questionnaires and receiving of answers that may be partly or fully processed via the software of the mobile device 402, or may be partly or fully processed on a backend server (illustrated in FIG. 11). In an example, the interface 408B includes a group of color coded regions 406. In one instance, the group of color coded regions 406 may correspond to the second group of color coded regions 330 in FIG. 3B. In another instance, the group of color coded regions 406 may correspond to a first group of color coded regions of interface 200. In addition, based in part on assessment previously performed, various forms of content as illustrated in the user interface of FIGS. 4, 5, and 6 may be provided to indicate various improvements available to the individual or group. In an addition aspect, some of the content of the interfaces 408A, 408B, and 408C may be aggregated content and suggested apps and content from other sources in the form of links for installation or detailed information provided as an excerpt using an application programming interface (API) of the suggested apps or from the other sources to access excerpts of content.

As in the case of the discussion with regards to FIG. 3B, the interface 408B provides related elements or traits to a selected element or trait 404. In addition, while interface 408B may be an overlay over the interface 408A, it may also be a new interface that replaces the interface 408A. Interface 408C provides still further information 410 upon selection of a related element or trait from the second group of color-coded regions 406. Each of the second group of color-coded regions 406 may be selectable, and some or all of the information 410 may be selectable. The selection may be by enabling the color-coded regions or information displayed in the present embodiments to include hyperlinks or selectable links supported by the underlying operating system such as Android® or iOS®.

In a similar manner as in FIG. 4, FIG. 5 displays information 504, 506, and 508 associated with the emotions or the behaviors upon selection from the third group of color-coded regions. In this example, the information 504, 506, and 508 includes one or more of text, images, audio, and video. The information 504, 506, and 508 may further describe exercises and or helpful pointers towards strengthening an element or trait. In an example, correspondences or interrelationships are also explained to provide the participant or participant with additional information that may be useful to adjust behaviors or emotions in a manner that the participant wishes.

FIG. 6 provides example interfaces for allowing a participant or entity to communicate portions or all of their experiences using the system and method to friends and/or colleagues or assessment professionals. As such, in the example of FIG. 6, Allison may be able to record a note associated with a sentiment towards the testing or with an answer to a question for a particular element using mobile device 602 and interfaces 606, 608. Allison may be able to then communicate 610 the recording to Cat's phone. Both Allison and Cat may either use an app incorporating the features of the system and method herein or may use a generic browser capable of rendering features of the system and method herein for notifying the participant of new changes or received information and for providing questions, receiving answer, and displaying assessments or results. Cat's phone 604 receives a notification that, when selected, may open inside the app or via the browser.

In an example, authentication is presumed to be provided, but a person of ordinary skill would recognize upon reading the present disclosure that Allison must have permitted Cat to be able to receive and review information for Allison's phone, or that the recording is not specifically tied to anything confidential or protected that Allison did not wish to share. When selected, the notification causes the app or the browser to display at least one color-coded region 614 and information 612 associated with the at least one color-coded region 614 or a link to open the recording provided. In an example, while recording is described in detail, Allison is also able to send a text message, video messages, and images for the app or the browser version of the app using a similar process flow as in the case of the recording described above. In an example, any communication between two or more participants or entities as to the testing may enable each of the two participants or entities to then provide an update to their independent testing. This is a form of random testing to update or dynamically change the prior testing. As this is not based on a predetermined time, but on a communication initiated between two participants, it provides a unique advantage of using additional information gathered from the communication to better a participant's involvement and ability to provide appropriate answers.

Figure 7:
FIG. 7 illustrates example portions of interfaces for displaying the flat three-dimensional representation of traits or elements in wearable devices to address small displays and limited memory issues in these devices, in accordance with an embodiment of the disclosure.

FIG. 7 provides example interfaces for allowing a participant or entity to actively communicate with other features of the present system and method. In this example, a wearable device 702 with limited display and memory capacity is used. In the case of a wearable device, notifications 704 are provided to the participant at discrete time intervals using a feature of the wearable device, such as a heart rate or pulse monitor. The pulse monitor of the wearable device is used in the present case to trigger the notification 704, which in turn allows the participant to select the notification and to review groups of color-coded regions of associated elements or traits to determine how to resolve the detected pulse elevation issue. Any information then provided by the participant is then usable to dynamically change or update the first group of color-coded regions to properly reflect a sentiment that may have been different when initially entered as an input to a questionnaire by the same participant or entity. In this manner, the testing presently offered is not necessarily limited to questionnaires, but may be extended to longer or predetermined periods to ensure that a participant or entity is able to provide the most accurate answer to an initial question. Using health elements of a wearable device ensures that real experiences are monitored and that real experiences cause the participant to provide accurate updates to their testing—either ongoing or to a previously completed test. The notification is also so that the entire table of interface 200 is not required to be displayed. In particularly, in response to the selection of the notification, only the relevant group or elements may be provided in their respective color-coded regions 706 for the participant to review and to consider amending. In an example, the amount of pixels may be adjusted using a sliding interaction on one of the color-coded regions 706, for instance.

Figure 8:
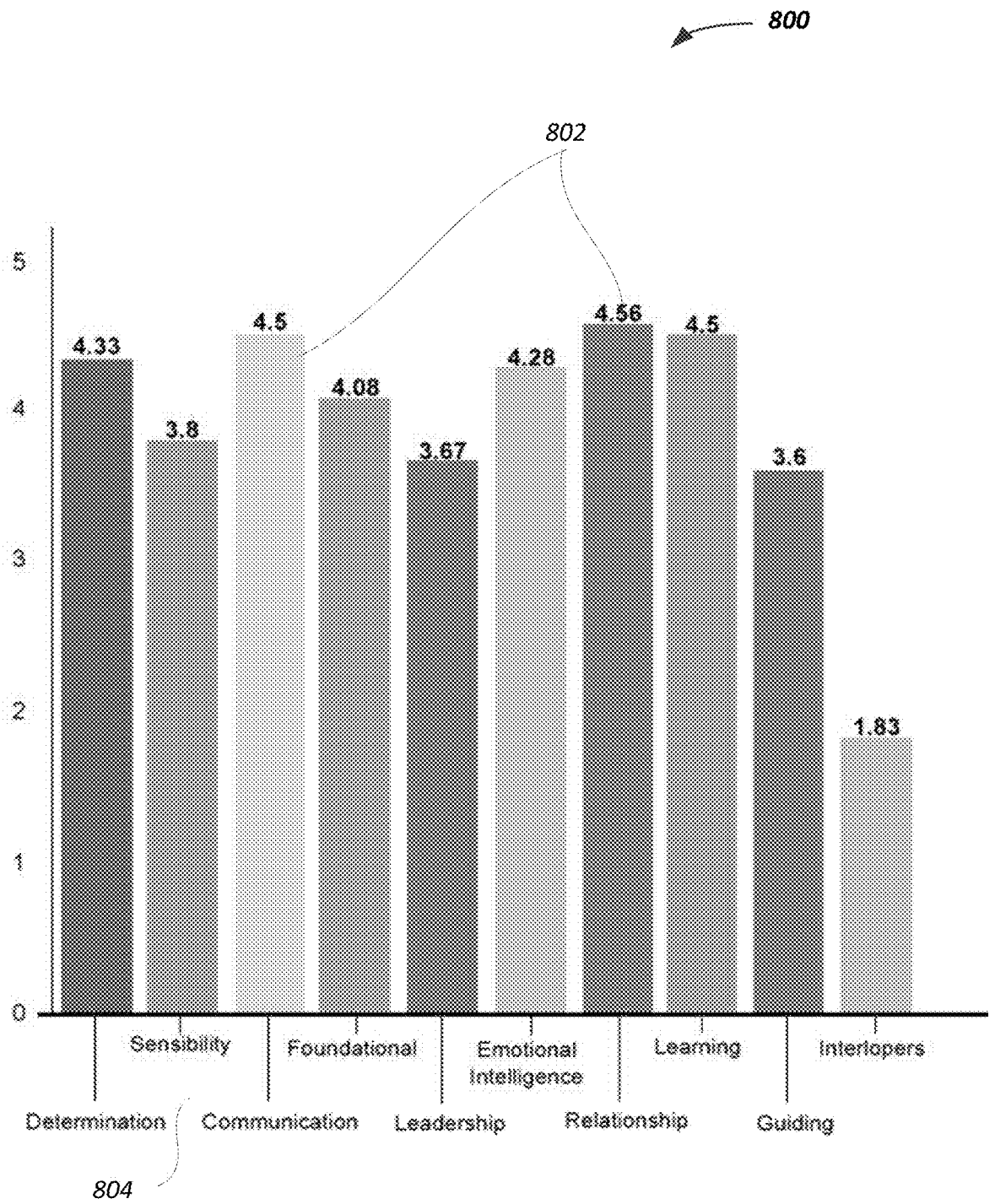
FIG. 8 illustrates an example portion of an interface with scores from assessments in each of the groupings of the traits or elements, in accordance with an aspect of an embodiment of the disclosure.

FIG. 8 provides a visual representation 800 of the scores calculated from numerical values assigned to elements, within each group, according to an embodiment. The visual representation 800 is also an example portion of an interface showing the scores from assessments of the groupings of the traits or elements. For example, the categories or groups 804 (also referred to as groups 510) include achievement, energy, communication, self care, emotional awareness, relationship, mindset, guiding, and stressors. Further aspects being included to the system herein are achievement, relationship, emotional intelligence, learning, doing, stressors. The scores are distributed among these categories and groups and the visual representation may be in other forms than the presently illustrated bar graph. The bar graph may show the score, or level associated with each emotion element category, on a scale of 0-5, according to an example. The scale, therefore, represents a common scale assigned to the categories or groups. As discussed throughout this disclosure, an overall score among the groups or categories may be calculated by averaging the individual scores 802 associated with each questionnaire answer, grouped according to the category. The overall score, in one instance, for a participant may be calculated according to the following formula:

$$\text{Overall score} = (\text{Achievement} + \text{Energy} +$$
$$\text{Communication} + \text{Self Care} + \text{Emotional Awareness} +$$
$$\text{Relationship} + \text{Mindset} + \text{Guiding} + \text{Stressors}) - (2.5 * \text{stressors}) + 16$$

In other embodiments, other scoring formulas may be used to calculate a personalized individual score, based on any number or combination of individual emotion elements and categories. The calculated score may be compared, by the processing system, to a score threshold in order to generate a behavior recommendation for the participant or entity. The score may represent a degree to which the stressors category of emotion elements or traits is detracting from the other, positive emotion elements. For example, as discussed above, scores between a first set of threshold points may be labeled evolved; scores between a second set of threshold points may be labeled on the move; scores between a third set of threshold points may be labeled coasting; scores between a fourth set of threshold points may be labeled struggling; and scores between a fifth set of threshold points may be labeled at risk. Furthermore, each of second threshold points in the first, the second, the third, the fourth, and the fifth sets of threshold points are contiguous or may include a spacing value therebetween. As such, a space value added to the high value of the fifth set may be the low value of the fourth set, and so on. As the fifth set represents the lowest set of values, the fourth set is above the fifth, the third is above the fourth, and so on.

In other embodiments, various score ranges and designations may be used. In the illustrated example, a participant's score is finally generated and may be provided offset from the graph of interface 800. In an example a score of 42.25 would place the participant within the on the move set of threshold points. Based on this identification, the participant may be provided with personalized recommendations for behavior and emotion element improvements and adjustments, including specific recommendations for overcoming problematic stressors identified as correspondence or interrelationships for the elements associated with the participant.

Figure 9B:
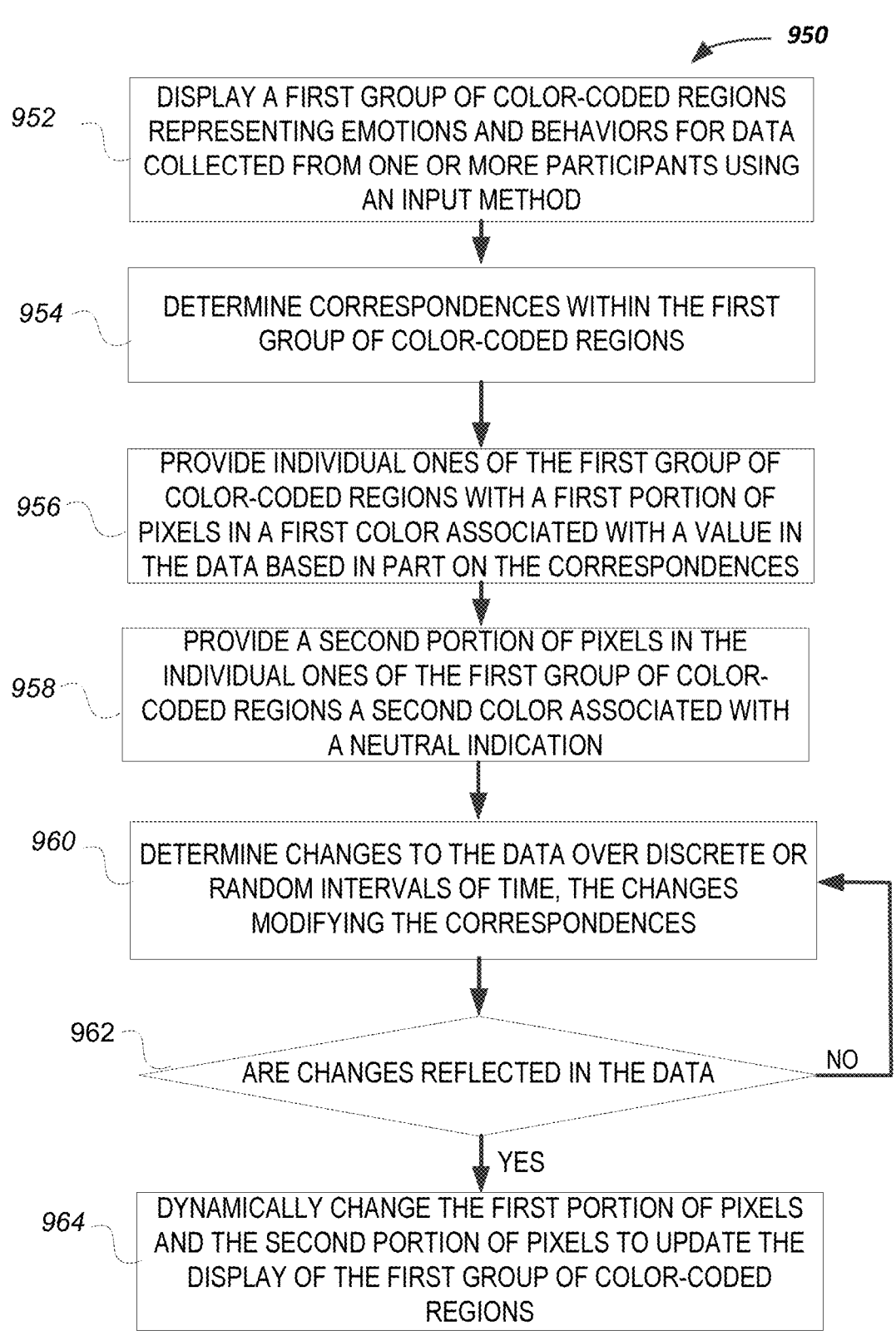

FIGS. 9A, 9B, and 9C illustrate flowcharts 900, 950, and 980 of example methods to achieve the interfaces for the flat three-dimensional representation of traits or elements. FIG. 9A provides a high level flowchart incorporating display and data management features of the present disclosure. The method of FIG. 9A begins with sub-process 902, which may be triggered by a supervisors, an administrator, or a participant. Sub-process 904 generates a human emotion element questionnaire that addresses questions unique to emotions and behavior of a participant or an entity of participants. Sub-process 906 is an input-output process for receiving data associated with the generated questionnaire. Sub-process 908 identifies the participant based at least in part on data that is part of the questionnaire. A categorizing function of sub-process 910 categorizes or sorts the data from sub-process 906 into the groups or categories described in the prior examples of FIGS. 2-8. In particular, sub-process 906 may be implemented as a mapping function for question numbers to an appropriate data structure holding groups or categories previously identified as counters to track the answer as respondent to one or more groups or categories.

Sub-process 914 assigns the data a respective numerical values, which is also understood as being assigned to particular elements or traits as these are part of the groups or categories for which the data is already categorized as in sub-process 910. For example, each answer may be assigned a respective numerical value, in some embodiments in a range of 1-5. The average numerical value of the questions within each emotion and behavioral category may then be calculated. For example, if question numbers 2, 16, 28, 62, and 63 each relate to the communication category of the identified emotion elements, the average numerical value of the answers provided to these questions may be calculated. The same average numerical value may be calculated for each of the other categories. The numerical values of each emotion and behavioral category may then be added together. The average numerical value for each question associated with the stressors category may be separately calculated and multiplied by a predetermined numerical factor, for example 2.5, to calculate the stressors impact as the correspondence or interrelationships in the data.

Sub-process 914 creates the visualization, such as a table, based in part on the numerical values to demonstrate the prominence of human emotion and behavioral categories in a participant's or participant entity makeup. This sub-process can include populating the data into color-coded regions which then defines the extent of the pixels to be assigned colors of the group or categories that the data falls within. Sub-process 916 calculates a score for each of the groups or categories based at least in part on the assigned respective numerical values from sub-process 912. For example, the stressors correspondence or interrelationship may be subtracted from the summed portion of the emotional and behavioral categories in order to compute an overall score for those categories and for the overall test. The calculated score of sub-process 916 may be indicative of a degree to which the stressors category answers impact the remaining categories of emotional and behavioral elements. This score may correspond to a category "level", indicating the amount of impact a certain category may have on the subject.

The calculated score for each of the plurality of individual emotion element categories may be presented to the participant in an interactive and appealing visual format as described with respect to the interfaces in FIGS. 2-8. For example, sub-process 918 may include populating the personalized table representation of the individual emotion elements based at least in part on the calculated score or level. In addition to FIGS. 2-8, an example chart is also illustrated and in FIG. 13. As such, the data visualization sub-process may generate the table with full or empty pixel assignments, while sub-process 918 then provides the values to populate the table. Sub-process 924 generates a display region for the participant, to provide the data visualization. In instances, the processes from 908-918 may be backend or processor-intensive operations, while the sub-process 924 may be a front-end display process.

In an example, a behavioral recommendation may be further provided based in part on the received questionnaire data via sub-process 922. For example, at sub-process 920, the flowchart 900 provides a feature for comparing the calculated score from sub-process 916 for each of the plurality of groups or categories to a predetermined score threshold. This may be the sets of thresholds previously described. For example, the calculated score may be compared to a behavioral analysis range, which may group numerical scores according to their behavioral status. Scores may be divided, according to an embodiment, into numerical ranges categorized as: evolved, on the move, coasting, struggling, and at risk. At sub-process 924, based in part on the score category to which the participant is assigned, the generated display may include a personalized plan for emphasizing positive elements and counteracting stressors elements. Such a plan may be provided as information underlying the displayed table, and particularly, underlying select elements or traits of the displayed table. The plan or portions thereof may be displayed upon selection of select elements or traits from the table, as illustrated by the processes in FIGS. 3A, 3B and 3-8. The information underlying the table may be provided to buffer in the participant's device to enable faster review and to manage the type of data provided to the device, depending on the type of device. For example, a wearable device having limited memory capacity may only be provided four highly scored elements or traits for display in color-coded regions of the wearable device. Information underlying at least one of the color-coded regions may be provided in the meantime to buffer and be prepared for when the participant selects to view information associated with the at least one of the color-coded regions.

In an example, the emotional and behavioral analysis of the present method and system may be tracked over a period of time, in order to identify changes, improvements, weaknesses, and the like. For example, sub-process 926 enables this after populating the personalized table displayed of the elements based at least in part on the calculated score as developed from a questionnaire. Particularly, the flowchart 900 includes an option to cycle back to step 906. A participant may be requested or may voluntarily input a secondary set of data associated with the generated questionnaire, as described using the examples of FIGS. 7 and 8. This is a dynamic process allowed in the present system and method, where updates are dynamic to the table using secondary input after one day, one week, one month, one year, or any other suitable period of time from the generation of the table. This may be random or discrete and may be initialized due to various processes caused by the participant—for e.g., an interaction with another participant of the present system and method providing a shared message or notification.

The secondary data may be categorized and assigned numerical values according to the sub-process 912 as discussed previously, and the display of the table for the identified participant may be updated dynamically to reflect this change. Sub-process 930 also illustrates an option for generating a comparative display for the participant to track to a date in time when the table was first generated and at various time points when updates were applied. Sub-process 928 generates one such comparative display, where the elements or traits for each participant or of related participants are provided. Aggregate community or team data in a participating entity may be used to analyze and understand emotions and behaviors present among various demographics, groups, or subgroups, and to identify correlations between various emotion elements. In an example, the generated table of elements and groups is compared to an update version that relies on the data. This comparative display may, therefore, be used to visualize changes in the participant's or entity's emotional or behavioral elements as part of the emotion. Any number of secondary data may be obtained at discrete or random intervals over time, in order to track emotional and behavioral changes, and such changes may be visually displayed in any number of comparative displays.

Analysis of comparison data over time may be used to provide specific steps and tangible ideas to advance cognitive behavioral therapy for individuals. These specific steps can be used to help individuals to better manage stressors and improve their well-being. Specific behavioral modifications, exercises, products, services, and the like can also be offered based on the comparison data. In a further example, community data may be obtained to identify trends, similarities, differences, and the like across multiple recipients within a team, company, group, demographic, or the like. For example, sub-process 926 enables data associated with the questionnaire to be obtained for related participants using such methods as the messaging process of FIG. 6 or the notification process of FIG. 7. In particular, the installation of the app or interest expressed by participants who are not yet participants may be used to activate monitoring elements (such as a health monitor) of a device hosting the app or features of the app.

FIG. 9B illustrates a flowchart 950 of another example method to achieve the interfaces for the flat three-dimensional representation of traits or elements. Sub-process 952 displays a first group of color-coded regions representing emotions and behaviors for data collected from one or more participants using an input method. Sub-process 954 determines correspondences within the first group of color-coded regions. As discussed previously, such a process may be applied from the assignment of numerical values, the scoring, and the calculating features of FIG. 9A. Sub-process 956 provides individual ones of the first group of color-coded regions with a first portion of pixels in a first color associated with a value in the data based in part on the correspondences. In an example, the table in interface 200 forms the first group of color-coded regions. Correspondences, used interchangeably with interrelationships, reflect the impact from at least one element or trait (e.g., the stressors) on other elements or traits in the table. This affects the number of pixels provided in the first color. Sub-process 958 provides a second portion of pixels in the individual ones of the first group of color-coded regions a second color associated with a neutral indication. For example, as illustrated in FIG. 2, elements may include a first color and second color in the color-coded regions such that the first color provides the level of involvement of a certain element based on the answers a participant or entity provided to a provided questionnaire.

Sub-process 960 determines changes to the data over discrete or random intervals of time, the changes modifying the correspondences. This may be associated with the secondary data discussed in reference to FIG. 9A. Sub-process 962 determines that changes are reflected in the data based on the secondary data, for instance. Sub-process 960 continues to determine changes if no change is reflected from sub-process 962. However, when a change is reflected in the data, then sub-process 964 dynamically changes the first portion of pixels and the second portion of pixels to update the display of the first group of color-coded regions. This process avoids having to provide multiple displays for smaller devices, but also avoids storing too much information on devices with limited allocated memory.

FIG. 9C illustrates a flowchart 980 of yet another example method to achieve the interfaces for the flat three-dimensional representation of traits or elements. Sub-process 982 generates data that includes interrelationships. The data includes data elements and individual ones of the data elements correspond to an assessment of one or more records. Sub-process 984 displays, in a display region of the multi-dimensional electronic interface, visual indicia from the data. The visual indicia include at least a first visual indicia being based on at least one of the data elements, a second visual indicia being based in part on the one or more records, and a third visual indicia being based in part on a common scale. A correlation exists within each of the first, the second, and the third visual indicia.

In an example, the first visual indicia may be an element of the table in interface 200. A single cell in the table may be the element. The second visual indicia may be a grouping of the elements based on the one or more records of a participant. A grouping or categorizing of cells in the table of interface 200 provides such a second visual indicia. The third visual indicia may be the level or numeric value assigned to the data element, which may be the common scale because the level or value may be represented off of a base value zero or range of values from zero to five as discussed in this disclosure with regards to FIG. 2. The visual indicia, therefore, includes data elements from different assessment based on the one or more records and based on the common scale. A correlation exists within each of the first, the second, and the third visual indicia. For example, one cell of the table, the group containing the cell, and the level of color within the cell all correlate to the cell. Sub-process 986 verifies if an interaction is detected for one of the visual indicia. Sub-process 988 displays a group of visual indicia responsive to an interaction with one of the visual indicia, where the visual indicia are positioned on the multi-dimensional electronic interface in a side-by-side arrangement to provide collective access of the data. Further, the group of visual indicia is presented with the plurality of visual indicia. This may be in the form of an overlay. The group of visual indicia may be fourth visual indicia that is provided in response to an interaction with at least one cell. For example, as the overlay on the table, and yet it is correlated to the at least one cell as well.

In the various embodiments of the disclosure described, a person having ordinary skill in the art will recognize that alternative arrangements of components, units, conduits, and fibers could be conceived and applied to the present invention. The present disclosure described herein, therefore, is well adapted to carry out the objects and attain the ends and advantages mentioned, as well as others inherent therein. While a presently preferred embodiment of the disclosure has been given for purposes of disclosure, numerous changes exist in the details of procedures for accomplishing the desired results. These and other similar modifications will readily suggest themselves to those skilled in the art, and are intended to be encompassed within the spirit of the present disclosure disclosed herein and the scope of the appended claims.

The singular forms "a," "an," and "the" include plural referents, unless the context clearly dictates otherwise.

Figure 10:
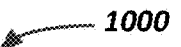
FIG. 10 illustrates an example system with example components that can be used to implement aspects of various embodiments of the disclosure.
Figure 10:
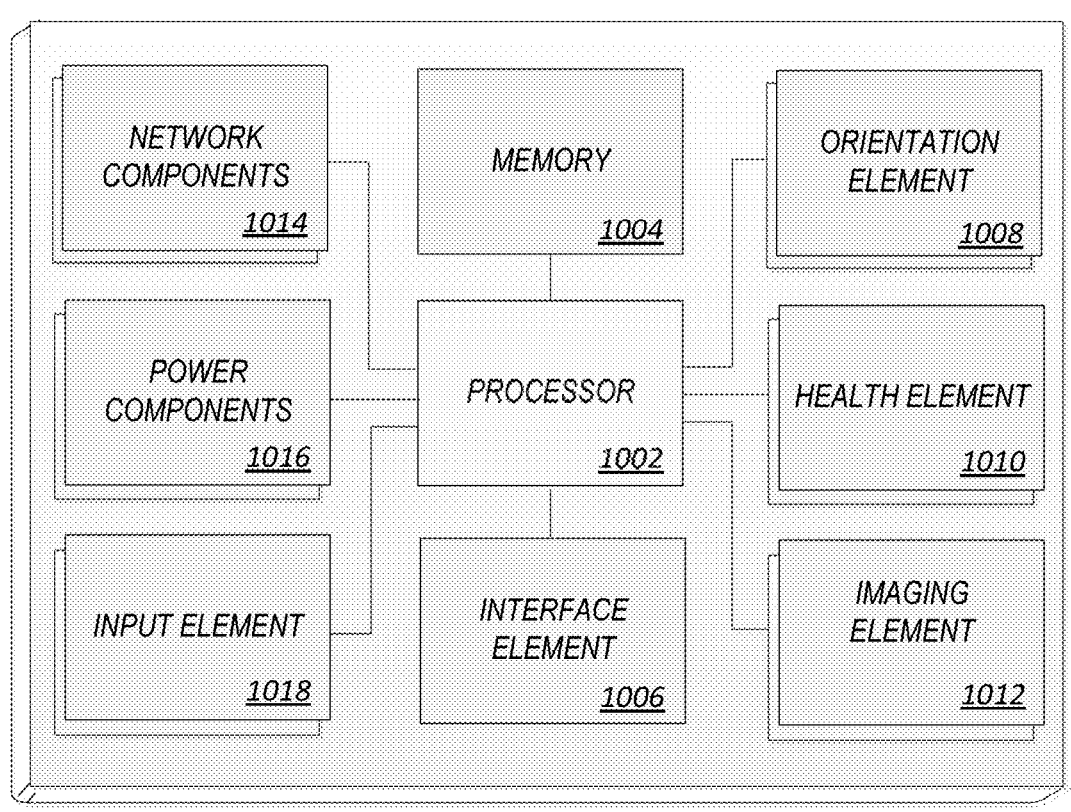

FIG. 10 illustrates a set of components of an example computing device 1000 that can be utilized to implement aspects of the various embodiments. Such a computing device 1000 may be used as the interactive device, the mobile device, or the wearable device described in the above examples. In this example, the device 1000 includes at least one processor 1002 for executing instructions that can be stored in a memory device or element 1004. As would be apparent to one of ordinary skill in the art, the device can include many types of memory, data storage or computer-readable media, such as a first data storage for program instructions for execution by the at least one processor 1002, the same or separate storage can be used for images or data, a removable memory can be available for sharing information with other devices, and any number of communication approaches can be available for sharing with other devices. The device 1000 may include at least one type of display element 1006, such as a touch screen, electronic ink (e-ink), organic light emitting diode (OLED) or liquid crystal display (LCD), although devices such as servers might convey information via other means, such as through a system of lights and data transmissions.

The device 1000 typically will include one or more networking components 1014, such as a port, network interface card, or wireless transceiver that enables communication over at least one network. The device 1000 can include at least one input element 1018 able to receive conventional input from a participant. This conventional input can include, for example, a push button, touch pad, touch screen, wheel, joystick, keyboard, mouse, trackball, keypad or any other such device or element whereby a participant can input a command to the device. These I/O devices for the input element 1018 could even be connected by a wireless infrared or Bluetooth or other link as well in some embodiments. In some embodiments, however, such a device might not include any buttons at all and might be controlled only through a combination of visual and audio commands such that a participant can control the device 1000 without having to be in contact with the device. In an example, the display element 1006 works together with the input element to provide a multi-dimensional electronic interface capable of providing display and receiving input, for instance.

The device 1000 may also include one or more imaging elements 1012 for performing the scans and capturing images as required. One or more orientation elements 1008 may be used to determine the orientation of the device, for example in relation to a participant's face or eyes. Various camera-based and other sensors, as part of the imaging element 1012, may be used to determine orientation. An orientation element 1008 can determine the position of the device. The orientation element 1008 can use one or more of GPS, local network detection, Bluetooth connection, or other protocols. One or more input elements 1018 can register participant input, for example input received from a touch screen display. An example device 1000 will also include power components 1016 and wireless ability in network components 1014 to communicate with other devices wirelessly.

Devices like device 1000 can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Device 1000 also includes a health element 1010 to perform health monitoring, such as pulse detection and hear rate monitoring aspects discussed with regards to the methods in FIGS. 2-9C. Alternatively, device 1000 shares some functions with a network server, which is discussed in FIG. 11. The imaging element 1012 provides imaging options to capture a participant's answers from written notes, if required. That data may be then provided to the device 1000 for processing in the processor 1002. Such a process avoids latency of high load data transfer and efficiently uses the resources available to the professional to incorporate certain features on the participant's side than on the server.

Figure 11:
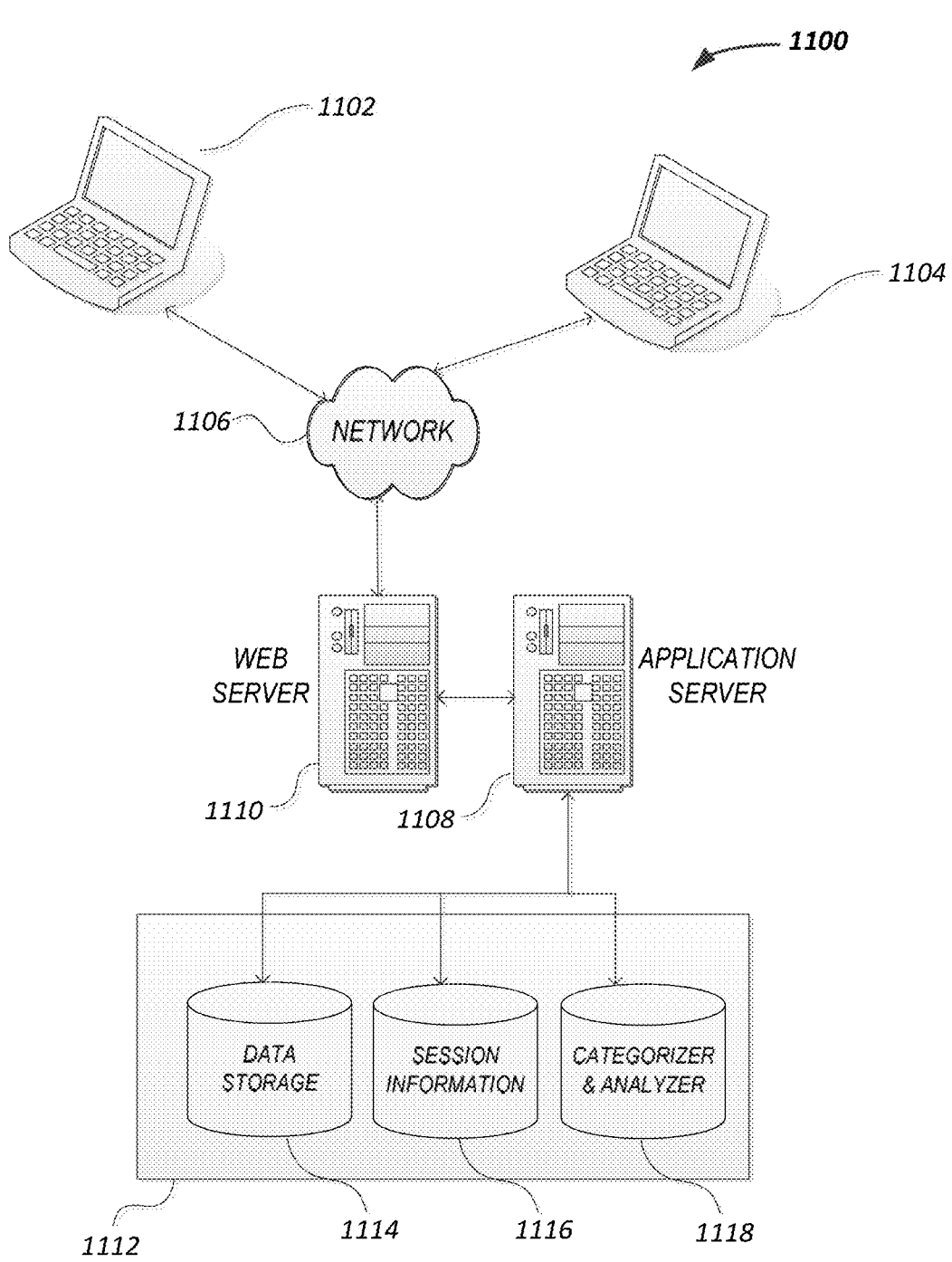
FIG. 11 illustrates an example system environment that can be used to implement aspects of various embodiments of the disclosure.

FIG. 11 illustrates an example system environment 1100 that can be used to implement aspects of various embodiments. The illustrative environment 1100 includes at least one application server 1108, a web server 1110, and a data store 1112. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server 1108 can include any appropriate hardware and software for integrating with the data store as needed to execute aspects of one or more applications for the client device and handling a majority of the data access and business logic for an application. The application server 1108 provides access control services in cooperation with the data store and is able to generate content such as text, graphics, audio and/or video to be transferred to the participant, which may be served to the participant by the Web server in the form of HTML, XML or another appropriate structured language in this example. The handling of all requests and responses, as well as the delivery of content between the client device and the application server, can be handled by the Web server 1110. It should be understood that the Web server 1110 and application servers 1108 are merely example components, as structured code discussed herein can be executed on any appropriate device or host machine as discussed elsewhere herein.

The data store 1112 can include several separate data tables, databases or other data storage mechanisms and media 1114-1118 for storing data relating to a particular aspect. For example, the data store 1112 illustrated includes mechanisms for storing content such as a data storage, session information storage, and a categorizer and analyzer 1114-1118. The session information may correspond to participant and profile information, which can be used to serve content for the production side. The data store 1112 is also shown to include the session information mechanism 1116 for storing log or session data. It should be understood that there can be many other aspects that may need to be stored in the data store, such as page image information and access rights information, which can be stored in any of the above listed mechanisms as appropriate or in additional mechanisms in the data store. The data store 1112 is operable, through logic associated therewith, to receive instructions from the application server and obtain, update or otherwise process data in response thereto. In one example, a participant might submit answers via the input in the client device 1102, 1104. In this case, the data store 1112 might access the participant's information from the answers to verify the identity of the participant and to access the data storage or session information to obtain information about status of the participant's testing. The information can then be returned to the participant, such as in a results listing on a Web page that the participant is able to view via a browser on the participant device. Information for a particular item of interest can be viewed in a dedicated page or window of the browser.

Each server 1110, 1108 typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment 1100 in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated. Thus, the depiction of the systems herein should be taken as being illustrative in nature and not limiting to the scope of the disclosure.

The various embodiments can be further implemented in a wide variety of operating environments, which in some cases can include one or more participant computers or computing devices 1102 and 1104 which can be used to operate any of a number of applications. Participant or client devices 1102 and 1104 can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network 1106 that would be familiar to those skilled in the art for supporting communications using any of a variety of commercially-available protocols, such as TCP/IP, FTP, UPnP, NFS, and CIFS. The network 1106 can be, for example, a local area network, a wide-area network, a virtual private network, the Internet, an intranet, an extranet, a public switched telephone network, an infrared network, a wireless network and any combination thereof.

In embodiments utilizing a Web server 1110, the Web server can run any of a variety of server or mid-tier applications, including HTTP servers, FTP servers, CGI servers, data servers, Java servers and business application servers. The server(s) may also be capable of executing programs or scripts in response requests from participant devices, such as by executing one or more Web applications that may be implemented as one or more scripts or programs written in any programming language, such as Java®, CC# or C++ or any scripting language, such as Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment 1100 can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, magnetic tape drives, optical storage devices and solid-state storage devices such as random access memory (RAM) or read-only memory (ROM), as well as removable media devices, memory cards, flash cards, etc.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

As discussed, different approaches can be implemented in various environments in accordance with the described embodiments. As will be appreciated, although a Web-based environment is used for purposes of explanation in several examples presented herein, different environments may be used, as appropriate, to implement various embodiments. The system includes an electronic client device, which can include any appropriate device operable to send and receive requests, messages or information over an appropriate network and convey information back to a participant of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server for receiving requests and serving content in response thereto, although for other networks, an alternative device serving a similar purpose could be used, as would be apparent to one of ordinary skill in the art.

The specification and drawings are, accordingly, to be regarded in an illustrative rather than a restrictive sense. It will, however, be evident that various modifications and changes may be made thereunto without departing from the broader spirit and scope of the invention as set forth in the claims.

Figure 12:
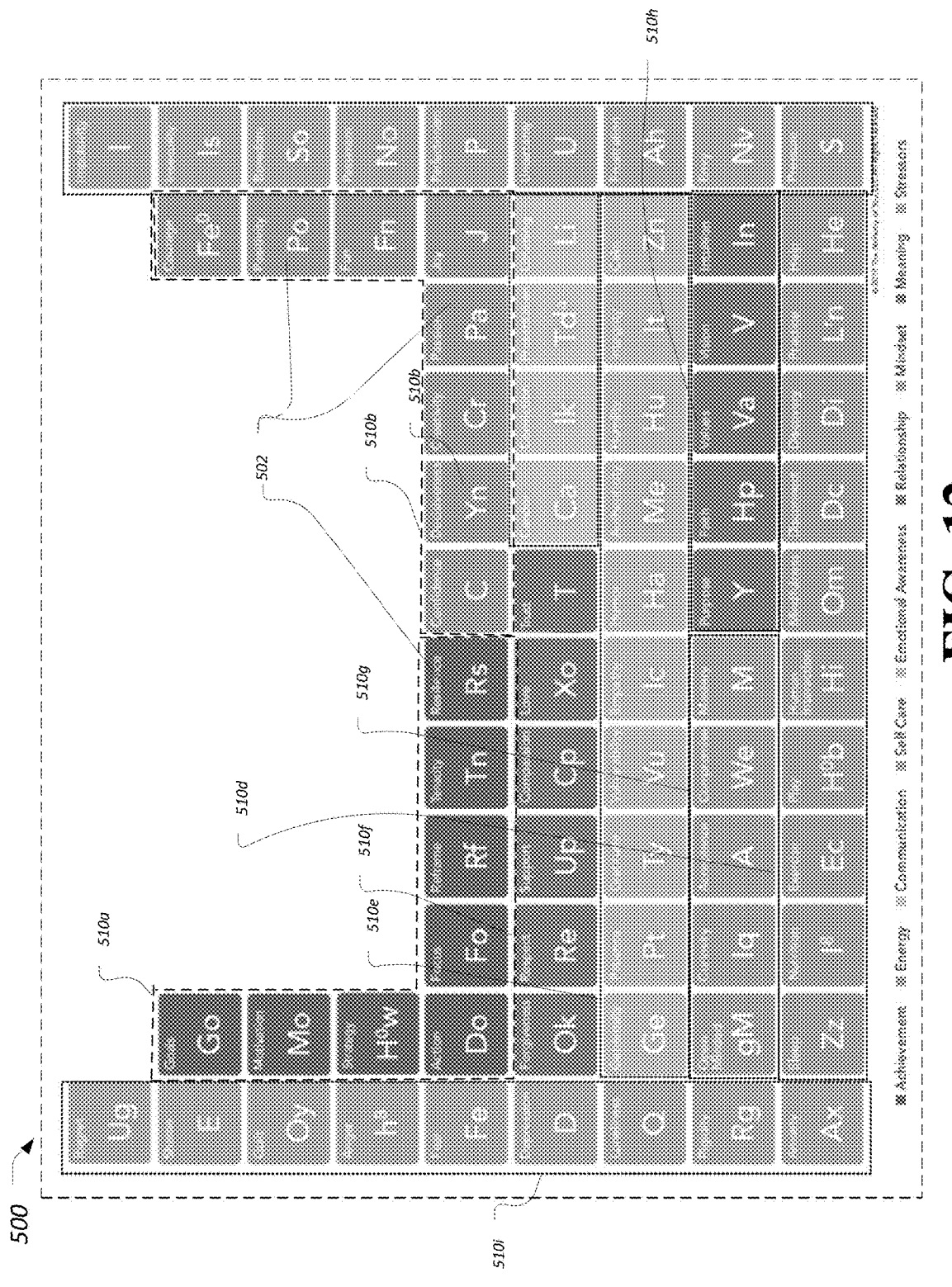
FIG. 12 illustrates an example element table.

FIG. 12 illustrates an example element table 500 including a plurality of personality categories 502 represented by the visual indicia or individual blocks. The personality categories 502 may include feelings or traits such as emotional intelligence, shame, curiosity, etc. These categories 502 may be arranged into various groups 510, including stressors and non-stressor. Each group 510 may be delineated from another by color. An achievement group 510*a* may be indicated by a first color. An energy group 510*b* may be indicated by a second color. Similarity, a communication group 510*c*, self care group 510*d*, emotional awareness group 510*e*, relationship group 510*f*, mindset group 510*g*, guiding group 510*h*, and stressors group 510*i* may each be indicated by a different color. The stressor group 510*i* may be referenced herein with respect to personality traits or elements that lead to stress. The remaining groups (e.g., groups 510*a-h*) may be referenced herein with respect to non-stressors.

The achievement group 510*a* may include categories 502 that dictate one's ability to remain committed to and accomplish goals. These categories 510 may be identified by the color red, since red is often the color of energy, ambition and determination.

The energy group 510*b* may include categories 502 that relate to spirit and demeanor, how a subject approaches a project, other people, and the world at large. These categories 510 may be identified by the color orange, for its ability to be uplifting and inspire positivity, as well as increase creativity.

The communication group 510c may include categories 502 that relate to the ability to express thoughts, ideas, and feelings to others. These categories 510 may be identified by the color yellow, for its relation to clarity of thought and new ideas.

The self care group 510d may include categories 502 that represent factors contributing to physical health and activities contributing to well-being. These categories 502 may be indicated by the color green to represent heath, youth, vigor, and renewal.

The emotional awareness group 510e may include categories 502 that relate to how one regulates emotions and understands the feelings of others. These categories 502 may be indicated by the color light blue to symbolize understanding, tranquility, and softness.

The relationship group 510f may include categories 502 that relate to traits that are validating and supportive of relationships. These categories 502 may be represented by the color bright pink to be associated with giving and receiving care.

The mindset group 510g may include categories 502 that relate to traits that impact mental and emotional agility. These categories may be represented by the color lavender to represent wisdom.

The guiding group 510h may include categories 502 relating to traits that reinforce one's ability to stay connected to what is important to you. These categories 502 may be represented by the color purple to represent spirituality and higher purpose.

The stressors group 510i may include categories 502 relating to traits or events that create strain in one's life. Stressors are not always negative in nature, as such events can also be inspiring, propel one to challenge oneself, and achieve new thresholds of capacity. These categories 502 may be represented by gray to illustrate a sense of discomfort, leading to a cloudy and unclear sense.

Figure 13:
FIG. 13 illustrates another example element table with various category levels.

FIG. 13 illustrates another example element table 600. The table 600 may be a personalized table 600 configured to illustrate a "level" of each element. The process behind the generation of the table is described above with respect to steps 912-918 of FIG. 9. The example table 600 may be generated based on an aggregation of data. This may include interpreting responses to a questionnaire provided to the subject. The data may also include various other data, particularly from third parties. Such data may include testing results such as those from Myers-Briggs Type Indicator® (MBTI®), DiSC® test, etc. The aggregation may provide multi-faceted, more in-depth results.

As explained, the level (or numerical score as previously explained) may be indicated by the fill level of that element. For example, in the example of FIG. 13, the laughter Ha category may be completely full, but the humility Hu category may be near empty. Each category 502 may still be represented by the associated color of the group 510, but the level may be indicated by the height of the color within that category.

The fill color may correspond to the impact that the category is having on the subject's emotional make-up. For example, laughter Ha may greatly affect the current emotional state of the subject, while humility Hu may not. These levels may help identify categories for which the subject may wish to improve, reflect on, etc.

Upon generation of the table 600, a report may also be generated based on the aggregated data. The report may include findings as to the respective levels of each category and group, as well as provide recommendations on steps the subject may take to minimize stressors and further activate categories and actions that may lead to a greater sense of well-being. The visual reports and tables aid the subject and others in understanding a subject's attitudes and behaviors and how each impact feelings and outcomes.

The report may highlight the categories 502 with strong, or high levels, as well as those with weak or low levels. The report may also highlight the groups 510 that have higher levels, as well as those groups 510 with lower levels. The report may also indicate how negativity is impacting the categories 502. This may highlight a certain group 510 that is brining levels down, as well as individual categories. For example, the report may indicate, "negativity is undermining your confidence C and potentially allow insecurity Is to seep in." Further, the report may state, for example, that "this is in turn likely holding you back from accomplishing your goals by reducing your grit Gr." "Focus on increasing your self compassion Cp." These are just example excerpts from a possible report. Infinite suggestions and combinations may be reported based on the aggregated data.

The table 600 may be interactive in that upon selecting one of the categories 502, additional display elements may be presented. This is discussed in detail above. This interactive table 600 may allow for an easy to use user experience, and supplement the report provided about the subject. In some example, suggestions on how to increase a level or actions to take in response to a certain category score may be provided. This may include literature, action items, etc., relating to that category. For example, upon selecting the category associated with anxiety Ax, a link to blog post or article relating to dealing with anxiety may be presented. Other forms of additional display elements may include links for professional services, such as professionals or support groups, as well as simple suggestions relating to that category. Some of the suggestions may mimic those presented as part of the report.

Figure 14:
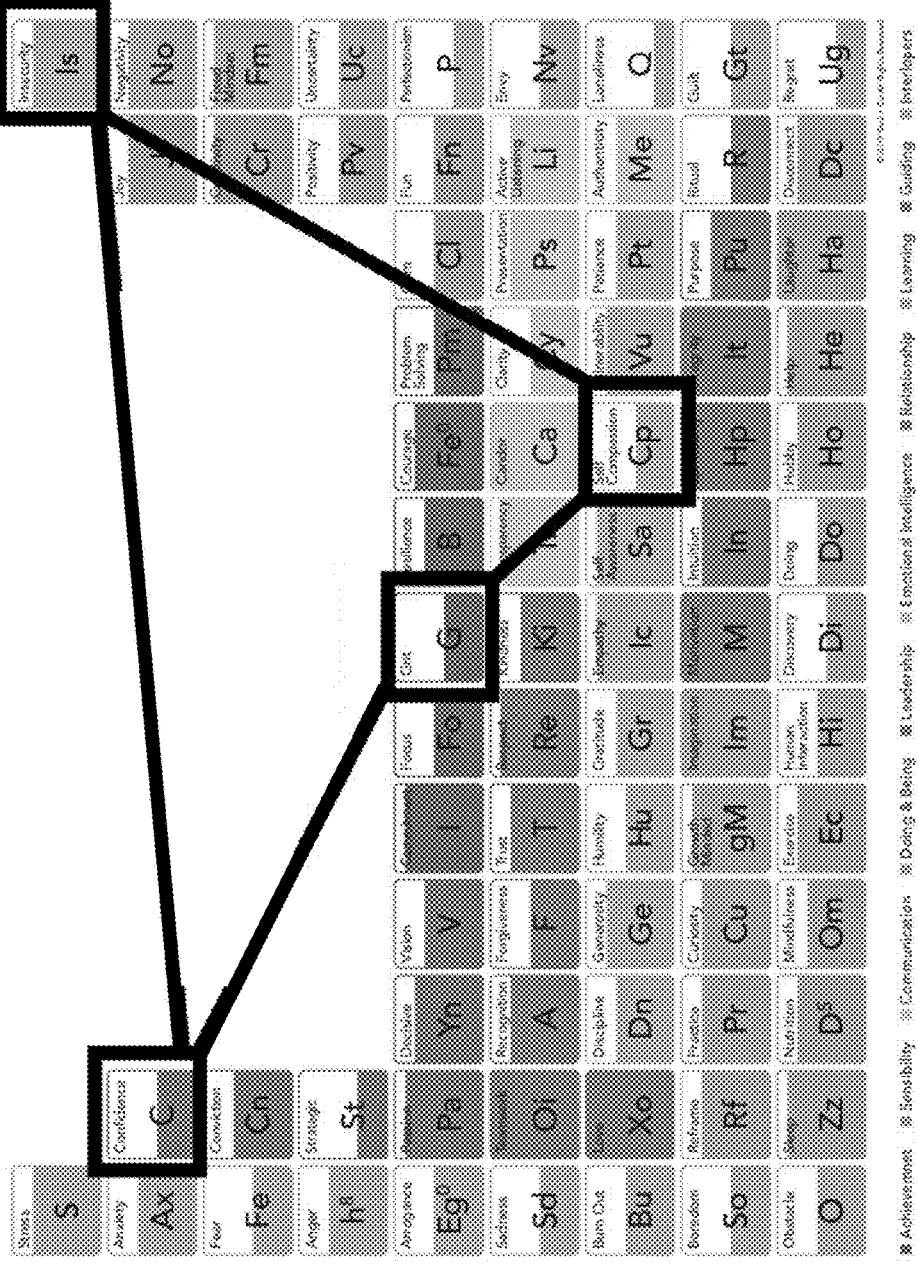
FIG. 14 illustrates another example element table with linked categories highlighted.

FIG. 14 illustrates another example table 700 with certain categories 502 linked. As explained above, certain stressors may correlate to a depletion in one or more categories. A single stressor may cause the level to drop in more than one category 502. Stressors with higher levels may have a greater affect on other non-stressors. If a stressor is above a fill level threshold, then that stressor may be considered to be a significant stressor. Furthermore, if a stressor affects a certain number of other non-stressors, the stressor may be considered a significant stressor. By addressing this stressor, levels of the affected non-stressors may be increased. Conversely, non-stressors that have a level below the fill level threshold may be considered at-risk categories, or categories that could use improvement to reach overall personal and behavioral satisfaction. The fill level threshold may be a threshold of 50%.

As shown in the example in FIG. 14, insecurity Is may affect self compassion Sc, grit G, and confidence C. The report may indicate correlations between stressors and affected categories. Such a correlation may be especially relevant to the analysis of the subject. It may explain how one stressor category effects multiple other categories. The report may allow the reader to easily identify which stressors are most relevant to the subject. The report may also identify which categories may increase their level or score. By addressing the stressor, the subject may therefore address the low level categories affected by the same. This may lead to an increase in emotional and behavioral satisfaction.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An interactive system comprising:
a multi-dimensional electronic interface; and
at least one processor configured to;
    receive data elements corresponding to an assessment of one or more records;
    display a plurality of visual indicia derived from the data elements, the plurality of visual indicia including interpersonal categories, each belonging to a group,
    receive a selection of one of the visual indicia, and
    present an overlay over at least a portion of the plurality of visual indicia, the overlay providing status data related to the data element associated with the selected visual indicia, the status data including information based on the assessment's correspondence to the selected visual indicia.

2. The system of claim 1, wherein the overlay provides interrelationships of the data elements to the selected visual indicia by displaying a subset of the plurality of visual indicia associated with the interrelated ones of the data elements within the overlay.

3. The system of claim 2, wherein each the subset of visual indicia identifies a level of impact identified by an amount of pixels within the visual indicia assigned to a first color.

4. The system of claim 3, wherein the level of impact of each of the subset of visual indicia is dynamically updated to reflect a specific relationship with the element of the selected visual indicia.

5. The system of claim 1, wherein the overlay is a partially transparent window configured to overlay over at least a portion of the plurality of visual indicia.

6. The system of claim 1, wherein the processor is further programmed to provide each group of the visual indicia with a first portion of pixels in a first color associated with a value in the data element based in part on a correspondences of that visual indicia with the group, and to provide a second portion of pixels in a second color associated with a neutral indication.

7. The system of claim 6, wherein the processor is further programmed to dynamically change the first portion of pixels in the first color based in part on a change to the data element using an input method, wherein the dynamic change to the first portion of pixels causing more or less first pixels to be associated with the first color and causing more or less second pixels to be associated with the first color.

8. A method for generating a personalized grouping of individual elements for visual identification, comprising:
    receiving data elements corresponding to an assessment of one or more records;
    displaying a plurality of visual indicia derived from the data elements, the plurality of visual indicia including interpersonal categories, each belonging to a group,
    receiving a selection of one of the visual indicia, and
    presenting an overlay over at least a portion of the plurality of visual indicia, the overlay providing status data related to the data element associated with the selected visual indicia, the status data including information based on the assessment.

9. The method of claim 8, wherein the overlay provides interrelationships of the data elements to the selected visual indicia by displaying a subset of the plurality of visual indicia associated with the interrelated ones of the data elements within the overlay.

10. The method of claim 9, wherein each the subset of visual indicia identifies a level of impact identified by an amount of pixels within the visual indicia assigned to a first color.

11. The method of claim 10, wherein the level of impact of each of the subset of visual indicia is dynamically updated to reflect a specific relationship with the element of the selected visual indicia.

12. The method of claim 8, wherein the overlay is a partially transparent window configured to overlay over at least a portion of the plurality of visual indicia.

13. The method of claim 8, further comprising providing each group of the visual indicia with a first portion of pixels in a first color associated with a value in the data element based in part on a correspondence of that visual indicia with the group, and to provide a second portion of pixels in a second color associated with a neutral indication.

14. The method of claim 13, further comprising dynamically change the first portion of pixels in the first color based in part on a change to the data element using an input method, wherein the dynamic change to the first portion of pixels causing more or less first pixels to be associated with the first color and causing more or less second pixels to be associated with the first color.

15. A device for an interactive personality system, comprising:
    a display;
    at least one processor; and
    memory comprising instructions that, when executed by the at least one processor cause the device to:
    receive data on at least one participant;
    determine a score for each category of a plurality of categories based on received data, wherein the plurality of categories relate to emotions and behaviors,
    display a plurality color-coded regions including individual blocks, wherein the individual blocks for the plurality color-coded regions represents the categories and indicates the score of the respective category, and
    present an overlay over the color-coded regions, the overlay providing status data including further information relating to at least one of the individual blocks.

16. The device of claim 15, wherein the processor is further configured to determine a correspondence between at least one category with at least one other category.

17. The device of claim 16, wherein the score indicates the correspondence between the at least one category with at least one other category.

18. The device of claim 15, wherein at least one of the categories is a stressor category affecting at least two other non-stressor categories.

19. The device of claim 15, wherein the score is identified by a fill level within the individual block.

20. The device of claim 19, wherein the processor is further configured to identify a stressor category as a significant stressor in response to the fill level of the respective stressor category exceeding a predefined fill level, wherein the non-stressor categories have a fill level below a fill level threshold and the stressor category has a fill level above the fill level threshold.

* * * * *